United States Patent [19]

Corbet et al.

[11] Patent Number: 4,590,004
[45] Date of Patent: May 20, 1986

[54] PRISTINAMYCIN DERIVATIVES, THEIR PREPARATION AND THEIR USE

[75] Inventors: Jean-Pierre Corbet, Ecully; Claude Cotrel, Paris; Daniel Farge, Thiais; Jean-Marc Paris, Vaires sur Marne, all of France

[73] Assignee: Rhone-Poulenc Sante, Courbevoie, France

[21] Appl. No.: 630,284

[22] Filed: Jul. 12, 1984

[30] Foreign Application Priority Data

Jul. 13, 1983 [FR] France .................. 83 11707

[51] Int. Cl.[4] .............................................. C07K 5/12
[52] U.S. Cl. .................................................. 530/317
[58] Field of Search ............................. 260/112.5 R

[56] References Cited

PUBLICATIONS

J. Preu d'homne P. Tarridec et A. Belloc pp. 585–591 (1967).
Chem. Abstr. vol. 99, (1983) 212905.
Chem. Abstr. vol 76, (1972) 127404.
Chem. Abstr. vol. 63, (1965) 13408.

Primary Examiner—Delbert R. Phillips
Attorney, Agent, or Firm—Stevens, Davis, Miller & Mosher

[57] ABSTRACT

The invention provides new pristinamycin $II_B$ derivatives of the formula:

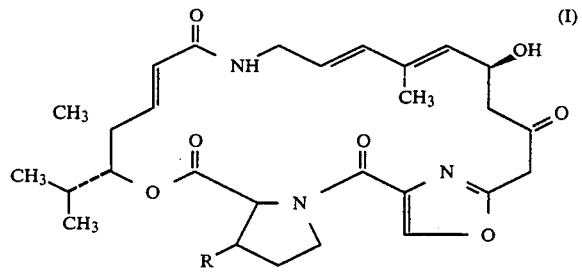

in which R represents alkylthio substituted by (i) alkylamino or dialkylamino of which the alkyl parts can form a pyrrolidin-1-yl, piperidino, azetidin-1-yl, azepin-1-yl, morpholino, thiomorpholino or piperazin-1-yl ring (optionally substituted by alkyl), or (ii) pyrrolidin-2-yl or pyrrolidin-3-yl, piperidin-2-yl, piperidin-3-yl or piperidin-4-yl, azetidin-2-yl or azetidin-3-yl or azepin-2-yl, azepin-3-yl or azepin-4-yl;
  a radical Het-S-, in which Het is pyrrolidin-3-yl, piperidin-3-yl or piperidin-4-yl, azetidin-3-yl or azepin-3-yl or azepin-4-yl optionally N-alkylsubstituted; or
dialkylamino of which the alkyl parts can form a pyrrolidin-1-yl, piperidino, azetidin-1-yl, azepin-1-yl, morpholino, thiomorpholino or piperazin-1-yl ring (optionally substituted by alkyl), the said alkyls having 1 to 5 carbon atoms each in a linear or branched chain. The compounds of the formula (I) are useful as antimicrobial agents when used in association with known synergistines or synergistines of the formula:

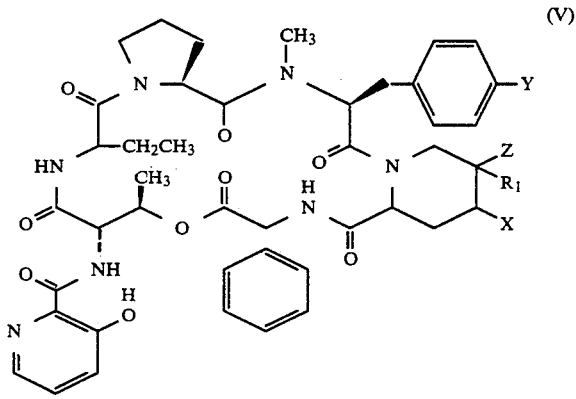

5 Claims, No Drawings

PRISTINAMYCIN DERIVATIVES, THEIR PREPARATION AND THEIR USE

This invention relates to synergistine derivatives and more particularly to derivatives of pristinamycin II$_B$.

The present invention provides new pristinamycin II$_B$ derivatives of the formula:

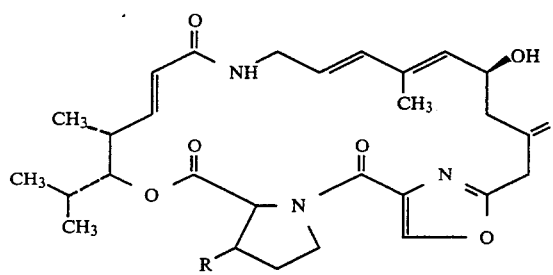

(I)

in which R represents an alkylthio radical substituted by:

(i) one or two alkylamino or dialkylamino radicals of which the alkyl parts can together optionally form, with the nitrogen atom to which they are bonded, a saturated heterocycle chosen from pyrrolidin-1-yl, piperidino, azetidin-1-yl, azepin-1-yl, morpholino, thiomorpholino and piperazin-1-yl (optionally substituted by an alkyl radical), or alternatively by:

(ii) a pyrrolidin-2-yl or pyrrolidin-3-yl, piperidin-2-yl, piperidin-3-yl or piperidin-4-yl, azetidin-2-yl or azetidin-3-yl or azepin-2-yl, azepin-3-yl or azepin-4-yl radical;

a radical of the formula:

Het—S—     (II)

in which Het represents an optionally N-alkylsubstituted pyrrolidin-3-yl, piperidin-3-yl or piperidin-4-yl, azetidin-3-yl or azepin-3-yl or azepin-4-yl radical; or a dialkylamino radical of which the alkyl parts can together optionally form, with the nitrogen atom to which they are bonded, a saturated heterocycle chosen from pyrrolidin-1-yl, piperidino, azetidin-1-yl, azepin-1-yl, morpholino, thiomopholino and piperazin-1-yl (optionally substituted by an alkyl radical), the aforesaid alkyl radicals and alkyl portions of radicals mentioned above or mentioned below containing 1 to 5 carbon atoms each in a linear or branched chain, and their salts.

The compounds of the formula (I) can have isomeric forms and these isomers and mixtures thereof fall within the scope of the present invention.

According to the present invention, the compounds of the formula (I) are prepared by reacting a compound of the formula:

R—H     (III)

in which R is defined as above, with a compound of the formula:

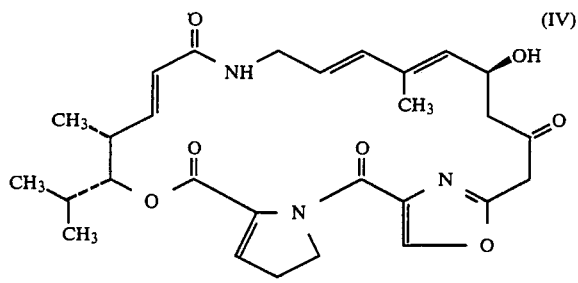

(IV)

i.e. pristinamycin II$_A$.

The reaction is generally carried out without a solvent or in an organic solvent such as an alcohol like methanol or ethanol or a chlorinated solvent like methylene chloride, 1,2-dichloroethane or chloroform, or in a mixture of these solvents (e.g. methylene chloride/methanol), at a temperature of between 0° and 50° C.

It can sometimes be advantageous to carry out the reaction in the presence of a tertiary amine, e.g. triethylamine, or an ethanolamine (e.g. dimethylethanolamine).

Those skilled in the art will understand that, if R represents a radical which contains a secondary amine group capable of interfering with the reaction, this group will have to be protected before the product of the general formula (III) is reacted with the product of the formula (IV). This can be effected using any customary means making it possible to block a secondary amine group in the form of a labile radical which can be removed after the reaction of the product of the general formula (III) with the product of the formula (IV). It is particularly advantageous to use the trifluoroacetyl radical as the blocking radical. This can then be removed using an aqueous solution of an alkali metal bicarbonate such as sodium bicarbonate or potassium bicarbonate.

The new products of the general formula (I) can be purified by the usual known methods, e.g. crystallization, chromatography or successive extractions in an acidic or basic medium. For those skilled in the art who are familiar with the sensitivity of synergistines to alkalis, the term "basic medium" is understood as meaning a medium which is just sufficiently alkaline to free the parent substance from its acid addition salt, i.e. a medium whose pH does not exceed 7.5 to 8.

It is well known that synergistines obtained by fermentation are useful in the treatment of many complaints due to Gram-positive bacteria (of the genus Staphylococcus, Streptococcus, Pneumococcus or Enterococcus) and Gram-negative bacteria (of the genus Haemophilus, Gonococcus or Meningococcus). However, these products have the disadvantage of being insoluble in an aqueous medium and they can therefore only be administered orally, generally in the form of capsules, coated tablets or ordinary tablets. In view of this insolubility, it is impossible to use the synergistines known hitherto if the patient is not capable of swallowing; this is the case in particular in paediatrics and intensive care, whereas the spectrum of activity of these products would make them a valuable indication in a large number of circumstances, e.g. in cases of comatose septicaemia.

The new products according to the invention have the considerable advantage of being able to be solubilized in water, generally in the form of salts, at usable therapeutic doses and of enhancing, by means of a synergism phenomenon, the antibacterial action of pristinamycin $I_A$, virginiamycin S or soluble synergistine derivatives of the general formula:

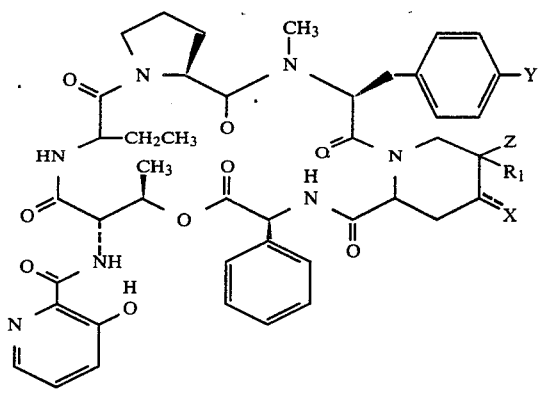

(V)

in which Y represents a hydrogen atom or a dimethylamino radical and (1) either ----- represents a single bond, Z and $R_1$ represent a hydrogen atom and X represents a radical of the general formula:

(VI)

in which:

$R_2$ represents a hydrogen atom and $R_3$ represents a hydroxyl radical or an alkyl radical optionally substituted by a carboxyl, alkoxycarbonyl or hydroxyl radical or by an alkylamino or dialkylamino radical of which the alkyl radicals can form, with the nitrogen atom to which they are attached, a 4-membered to 7-membered heterocycle chosen from azetidinyl, pyrrolidinyl, piperidinyl, piperazinyl, N-alkylpiperazinyl or azepinyl, or alternatively $R_3$ represents a cycloalkyl radical containing 3 to 7 carbon atoms or a saturated 4-membered to 7-membered heterocycle chosen from the azetidine, pyrrolidine, piperidine and azepine rings, it being possible for these heterocycles to be optionally substituted on the nitrogen atom by an alkyl radical, or $R_2$ represents a formyl or alkylcarbonyl radical and $R_3$ represents an alkyl radical substituted by a carboxyl radical or by an alkylamino or dialkylamino radical of which the alkyl radicals can form, with the nitrogen atom to which they are attached, a 4-membered to 7-membered heterocycle chosen from azetidinyl, pyrrolidinyl, piperidinyl, piperazinyl, N-alkylpiperazinyl or azepinyl, or alternatively $R_3$ represents a 4-membered to 7-membered heterocycle chosen from the azetidine, pyrrolidine, piperidine and azepine rings, it being possible for these heterocycles to be substituted on the nitrogen atom by an alkyl radical, or $R_2$ and $R_3$, which are identical or different, represent an alkyl radical optionally substituted by a carboxyl, alkoxycarbonyl or hydroxyl radical or by an alkylamino or dialkylamino radical of which the alkyl radicals optionally form, with the nitrogen atom to which they are attached, a 4-membered to 7-membered heterocycle chosen from azetidinyl, pyrrolidinyl, piperidinyl, piperazinyl, N-alkylpiperazinyl or azepinyl, or $R_2$ and $R_3$ together form, with the nitrogen atom to which they are attached, a 4-membered to 7-membered heterocycle chosen from the azetidine, pyrrolidine, piperidine, morpholine and piperazine rings and optionally substituted by an alkyl radical, (2) or alternatively ----- represents a double bond, X represents an oxygen atom and Z represents a radical of the general formula:

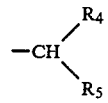

(VII)

defined in the following manner:

(a) either $R_1$ and $R_5$ each represent a hydrogen atom and $R_4$ represents a pyrrolidin-3-ylthio or piperidin-3-ylthio or piperidin-4-ylthio radical (these radicals being optionally substituted by an alkyl radical), or alternatively $R_4$ represents an alkylthio radical substituted by one or two hydroxysulphonyl radicals or alkylamino or dialkylamino radicals (optionally substituted by a mercapto or dialkylamino radical) or by one or two rings chosen from piperazino (optionally substituted by an alkyl or mercaptoalkyl radical), morpholino, thiomorpholino, piperidino, pyrrolidin-1-yl, piperidin-2-yl, piperidin-3-yl or piperidin-4-yl and pyrrolidin-2-yl or pyrrolidin-3-yl (these last two rings being optionally substituted on the nitrogen atom by an alkyl radical), (b) or $R_1$ and $R_5$ together form a valence bond and $R_4$ represents a pyrrolidin-3-ylamino, piperidin-3-ylamino or piperidin-4-ylamino, pyrrolidin-3-yloxy, piperidin-3-yloxy or piperidin-4-yloxy, pyrrolidin-3-ylthio, piperidin-3-ylthio or piperidin-4-ylthio radical (these radicals being optionally substituted on the nitrogen atom of the ring by an alkyl radical), or alternatively $R_4$ represents an alkylamino, alkoxy or alkylthio radical substituted by one or two hydroxysulphonyl radicals, alkylamino or dialkylamino radicals (optionally substituted by a dialkylamino radical) or trialkylammonio or imidazol-4-yl or imidazol-5-yl radicals or by one or two rings chosen from piperazino (optionally substituted by an alkyl or mercaptoalkyl radical), morpholino, thiomorpholino, piperidino, pyrrolidin-1-yl, piperidin-2-yl, piperidin-3-yl or piperidin-4-yl and pyrrolidin-2-yl or pyrrolidin-3-yl (these last five rings being optionally substituted on the nitrogen atom by an alkyl radical), it being understood that the alkyl radicals and alkyl portions relating to the symbols of the general formula (V) contain 1 to 5 carbom atoms and are in a linear or branched chain.

Some of the synergistine derivatives of the general formula (V) can have isomeric forms. It is understood that these isomeric forms and also mixtures thereof can advantageously be associated with the products of the general formula (I).

The products of the general formula (V) defined as above under 1), except for those in which $R_2$ represents a formyl or alkylcarbonyl radical, can be prepared by reacting an amine of the general formula:

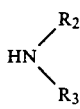

(VIII)

in which $R_2$ and $R_3$ are defined as above, with a synergistine of the general formula:

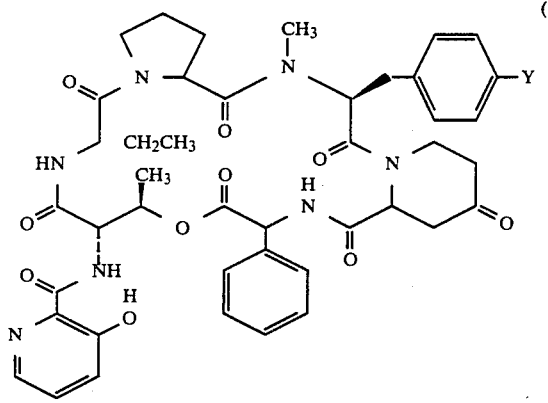

(IX)

in which Y represents a hydrogen atom (virginiamycin S) or the dimethylamino radical (pristinamycin $I_A$), in the presence of an alkali metal cyanoborohydride.

The reaction is generally carried out with an excess of amine of the general formula (VIII), in the presence of an alkali metal cyanoborohydride such as sodium cyanoborohydride, in an organic solvent, such as an alcohol, in which hydrogen chloride has been dissolved (methanol containing hydrogen chloride or ethanol containing hydrogen chloride), at a temperature of between 0° C. and the reflux temperature of the reaction mixture, preferably at a temperature of the order of 20° C.

The reaction can advantageously be carried out in the presence of a drying agent such as molecular sieves.

The products of the general formula (V) defined as above under (1) in which $R_2$ represents a formyl or alkylcarbonyl radical and $R_3$ represents an alkyl radical substituted by a carboxyl radical or by an alkylamino or dialkylamino radical of which the alkyl radicals optionally form, with the nitrogen atom to which they are attached, a 4-membered to 7-membered heterocycle chosen from azetidinyl, pyrrolidinyl, piperidinyl, piperazinyl, alkylpiperazinyl or azepinyl, or represents a saturated 4-membered to 7-membered heterocycle chosen from the azetidine, pyrrolidine, piperidine and azepine rings, it being possible for these heterocycles to be substituted on the nitrogen atom by an alkyl radical, and Y is defined as above, can be prepared by reacting a product of the general formula:

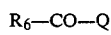 $R_6$—CO—Q (X)

in which $R_6$ represents a hydrogen atom or an alkyl radical and Q represents a halogen atom or an alkylcarbonyloxy radical, with a product of the general formula:

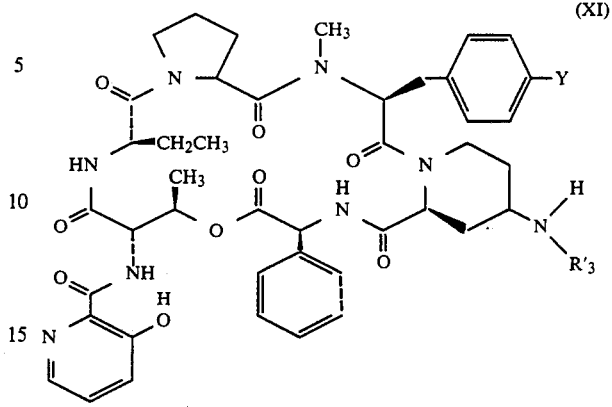

(XI)

in which Y is defined as above and $R'_3$ has the corresponding definition of $R_3$ given above.

The reaction is generally carried out in an organic solvent such as pyridine, a chlorinated solvent (methylene chloride) or an ether (tetrahydrofuran), in the presence of an acid acceptor such as an organic base like triethylamine or an inorganic base such as an alkali metal carbonate or bicarbonate like sodium bicarbonate, at a temperature of between 0° C. and 80° C.

Those skilled in the art will understand that, if $R'_3$ represents a radical containing a secondary amine group, the said group must be protected before the product of the general formula (X) is reacted with the product of the general formula (XI). This is effected using any customary blocking means employed for protecting an amine group and capable of being removed thereafter, without affecting the rest of the molecule. It is particularly advantageous to use the trifluoroacetyl radical as the blocking radical; this can then be removed using an aqueous solution of an alkali metal bicarbonate such as sodium bicarbonate or potassium bicarbonate.

Those skilled in the art will also understand that, if $R_2$ and/or $R_3$ in the general formula (VIII) represent a radical containing a secondary amine group, this must be protected before the product of the general formula (VIII) is reacted with the product of the general formula (IX). The blocking and unblocking are carried out as described above.

The products of the general formula (V) defined as above under (2) in which Y is defined as above and the other symbols are defined as above under (2) (a) can be prepared by reacting a product of the general formula:

 $R'_4$—H (XII)

in which $R'_4$ has the definition of $R_4$ given above under (2) (a), with a product of the general formula:

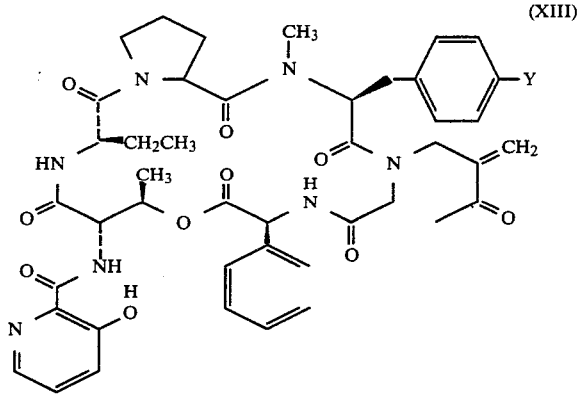

in which Y is defined as above.

The reaction is generally carried out in an organic solvent such as an alcohol like methanol or a chlorinated solvent like chloroform, or a mixture of these solvents, at a temperature of between 0° C. and the reflux temperature of the reaction mixture, preferably at a temperature of the order of 20° C.

The products of the general formula (XIII) can be prepared by reacting an alkali metal borohydride such as sodium cyanoborohydride with a product of the general formula:

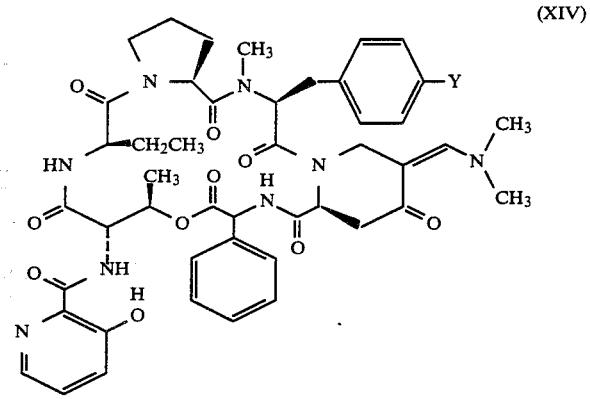

in which Y is defined as above.

The reaction is generally carried out in an organic solvent such as an ether like tetrahydrofuran or an alcohol, e.g. isopropanol, in the presence of an acid such as trifluoroacetic acid, at a temperature of between 0° C. and the reflux temperature of the reaction mixture, preferably at a temperature of the order of 20° C.

The products of the general formula (XIV) can be obtained by reacting a product of the formula:

in which either $X_1$ represents an alkoxy radical and $X_2$ represents an alkoxy or dimethylamino radical, or alternatively $X_1$ and $X_2$ both represent a dimethylamino radical, with a product of the general formula (IX).

In practice, it is advantageous to react tert.-butoxybis(dimethylamino)methane with the product of the general formula (IX), in an organic solvent such as a chlorinated solvent like 1,2-dichloroethane or an amide (e.g. dimethylformamide), at a temperature of between 0° C. and 80° C., preferably at a temperature of the order of 20° C.

The products of the general formula (XV) can be prepared according to the methods described by H. BREDERECK et al., Chem. Ber., 101, 41 and 3058 (1968) and Chem. Ber., 106, 3725 (1973).

The products of the general formula (V) in which Y is defined as above and the other symbols are defined as above under (2) (b), except that $R_4$ cannot represent a pyrrolidin-3-yloxy, piperidin-3-yloxy or piperidin-4-yloxy or alkoxy radical optionally substituted as defined under (2) (b), can be prepared by reacting a product of the general formula:

$$R''_4\text{—H} \qquad (XVI)$$

in which $R''_4$ has the definition of $R_4$ given above, with a product of the general formula (XIV) in which Y is defined as above.

The reaction is carried out in an organic medium, in the presence of an acid (e.g. acetic acid or a mixture of acetic acid and catalytic quantities of trifluoroacetic acid), in the presence or absence of a solvent, at a temperature of between 0° and 50° C., preferably at a temperature of the order of 20° C.

If necessary, the solvent can be chosen from organic solvents such as ethers (tetrahydrofuran), alcohols (ethanol) and chlorinated solvents (e.g. methylene chloride or chloroform).

The products of the general formula (V) in which Y is defined as above and the other symbols are defined as above under (2) (b) can be prepared by reacting a product of the general formula:

$$R'''_4\text{—H} \qquad (XVII)$$

in which $R'''_4$ is defined in the same way as $R_4$ under (2) (b), with a product of the general formula:

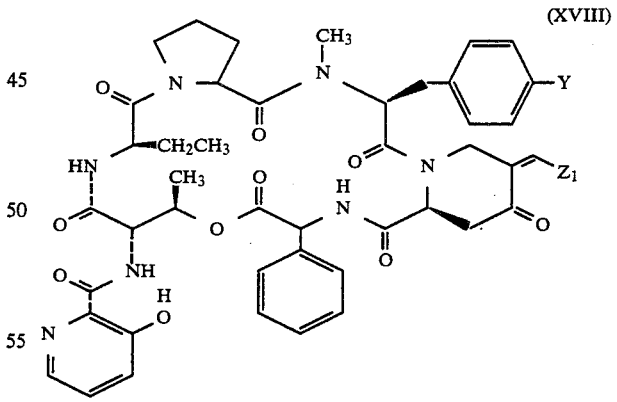

in which Y is defined as above and $Z_1$ represents a tosyloxy, acetyloxy or trimethylsilyloxy radical or a dialkoxyphosphoryloxy radical of which the alkyl parts contain 1 to 4 carbon atoms in a linear or branched chain, or alternatively $Z_1$ represents a chlorine atom.

The reaction is generally carried out in an organic solvent such as an ether like tetrahydrofuran, an alcohol like ethanol or a chlorinated solvent (e.g. methylene chloride or chloroform), at a temperature of the order of 20° C. The reaction is carried out in a basic medium, e.g. in the presence of an alkali metal hydride or an alkali metal alcoholate such as sodium ethylate or potassium tert.-butylate.

If R'''₄ is other than heterocyclyloxy or substituted alkoxy, the reaction can also be carried out either in a neutral medium at a temperature of between 0° and 50° C., in one of the solvents mentioned above, or in an acid medium under conditions identical to those described above for the reaction of a product of the general formula (XVI) with a product of the general formula (XIV).

The products of the general formula (XVIII) can be prepared by the acid hydrolysis of a product of the general formula (XIV) to give a product of the general formula:

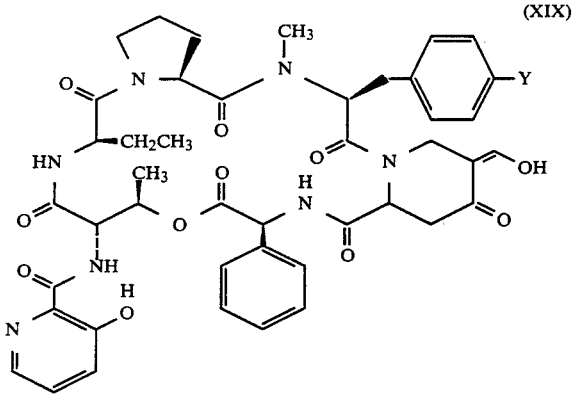

this being followed by:

(α) either reaction with a product of the general formula:

$$Z'_1—X \quad (XX)$$

in which X represents a halogen atom and $Z'_1$ has the definition given above for $Z_1$, except that it cannot represent a chlorine atom, (β) or reaction with a product of the formula:

$$(C_6H_5)_3PCl_2 \quad (XXI)$$

to give a product of the general formula (XVIII) in which $Z_1$ represents a chlorine atom.

The hydrolysis of the product of the general formula (XIV) to give the product of the general formula (XVIII) is carried out by means of an aqueous solution of a mineral acid such as a 0.1N aqueous solution of hydrochloric acid, the reaction temperature being about 20° C.

The reaction of the product of the general formula (XX) with the product of the general formula (XIX) is generally carried out in an organic solvent such as methylene chloride, in the presence of an acid acceptor such as an organic base like triethylamine or an inorganic base like an alkali metal carbonate or bicarbonate, e.g. sodium bicarbonate or potassium bicarbonate. The reaction temperature is generally between −20° and +20° C.

The reaction of the product of the general formula (XXI) with the product of the general formula (XIX) is generally carried out in a chlorinated solvent such as methylene chloride, at a temperature of between −20° and +20° C.

The products of the general formulae (III), (VIII), (XII), (XVI) and (XVII) can be prepared according to or by analogy with the methods described below in the examples, and especially according to:

G. G. Urquart et al., Org. Synth., 21, 36 (1941)

A. I. Vogel, J. Chem. Soc., 1822 (1948)

J. H. Chapman and L. N. Owen, J. Chem. Soc., 579 (1950)

H. R. Snyder et al., J. Am. Chem. Soc., 69, 2672 (1947)

D. D. Reynolds et al., J. Org. Chem., 26, 5125 (1961)

J. W. Haeffele et al., Proc. Sci. Toilét Goods Assoc., 32, 52 (1959)

H. Barrer et al., J. Org. Chem., 27, 641 (1962)

J. H. Biel et al., J. Amer. Chem. Soc., 77, 2250 (1955)

in the case of a product of the general formula (III), (XII), (XVI) or (XVII) in which R, R'₄, R''₄ or R'''₄ represents a heterocyclylthio or substituted alkylthio radical, or according to:

A. J. W. Headlee et al., J. Amer. Chem. Soc., 55, 1066 (1933)

B. K. Campbell and K. N. Campbell, J. Amer. Chem. Soc., 60, 1372 (1938)

R. C. Elderfield et al., J. Amer. Chem. Soc., 68, 1579 (1946)

in the case of a product of the general formula (XVI) or (XVII) in which R''₄ or R'''₄ represents a heterocyclyloxy or substituted alkoxy radical, or according to:

J. Amer. Chem. Soc., 54, 1499 (1932) and

J. Amer. Chem. Soc., 54, 3441 (1932)

in the case of a product of the general formula (VIII) or of the general formula (III), (XVI) or (XVII) in which R, R''₄ or R'''₄ are substituted alkylamino radicals, or according to:

E. F. Elslager et al., J. Med. Chem., 17, 99 (1974)

L. M. Werbel et al., J. Het. Chem., 10, 363 (1973)

in the case of a product of the general formula (III), (XVI) or (XVII) in which R, R''₄ or R'''₄ are heterocyclylamino radicals.

It is understood that, in the above methods, if $R_2$, $R_3$, R'₄, R''₄ or R'''₄ contains an alkylamino radical capable of interfering with the reaction, this is protected beforehand by any known method which does not affect the rest of the molecule.

Likewise, if the radicals R'₄, R''₄ and R'''₄ in the products of the general formulae (XII), (XVI) and (XVII) contain a secondary amine group capable of interfering with the reaction, this must be protected before the corresponding products are reacted with the products of the general formulae (XIII), (XIV) and (XVIII) respectively. The protecting radical is removed after the reaction. This is effected under the conditions described above for the radical R of the reactant of the general formula (III).

If necessary, the isomers of the products of the general formula (I) and/or of the products of the general formula (V) can be separated by chromatography or by high performance liquid chromatography.

The products of the general formula (V) can be purified in the manner mentioned above for the products of the general formula (I).

In the laboratory, the products of the general formula (I) have a synergistic effect on the antibacterial action of the products of the formula (V) at doses of between 5 and 200 mg/kg, administered subcutaneously to mice, especially in septicaemia caused by *Staphylococcus aureus* Smith, if they are mixed with the products of the general formula (V) in proportions varying between 10-90% and 90-10%.

The acute toxicity of the compounds of formula (I), expressed as the $LD_{50}$, is generally between 300 and 900 mg/kg, administered subcutaneously to mice.

Of particular value for their good synergistic effect towards pristinamycin $I_A$ are the compounds of formula (I) in which: R represents an alkylthio radical substituted by one or two dialkylamino radicals in which the alkyls can be joined to form, with the nitrogen atom to which they are attached, a saturated heterocycle chosen from pyrrolidin-1-yl and piperazin-1-yl unsubstituted or substituted by an alkyl radical; or R represents either a radical of the formula Het—S— in which Het represents an optionally N-alkyl substituted piperidin-4-yl radical, or a dialkylamino radical in which the alkyls can be joined to form, with the nitrogen atom to which are bonded, a piperazin-1-yl ring unsubstituted or substituted by an alkyl radical, the said alkyl radicals and alkyl portions of radicals being linear or branched and containing 1 to 3 carbon atoms each. Of more particular value among these compounds are those in which R is a branched alkylthio radical of 1 to 3 carbon atoms, substituted by a dialkylamino radical, or R represents a 4-alkylpiperazin-1-yl ring, the said alkyl radicals containing, except where otherwise stated, 1 or 2 carbon atoms each; and in particular the following compounds: 26-(1-diethylaminoprop-2-yl)thiopristinamycin $II_B$, and 26-(4-methylpiperazin-1-yl)pristinamycin $II_B$.

For use in therapy, the compounds of the invention can be employed as such, i.e. in the form of the base, in association with known synergistines, but as the main advantage of the new compounds is the possibility of dissolving them in water, it is particularly advantageous to use them in the form of pharmaceutically acceptable acid addition salts, in association with known synergistines or a synergistine of the formula (V), which may themselves be solubilized either in the form of a pharmaceutically acceptable salt or, if appropriate, in the form of the base if the solubility of the latter is sufficient for the resulting solution to contain a quantity of product which is at least equal to the therapeutically active dose.

Pharmaceutically acceptable salts which may be mentioned, both for the products of the general formula (I) and for the products of the general formula (V), are the addition salts with mineral acids, such as hydrochlorides, hydrobromides, sulphates, nitrates and phosphates, or with organic acids, such as acetates, propionates, succinates, maleates, fumarates, methanesulphonates, p-toluenesulphonates and isethionates, or substitution derivatives of these compounds. Other pharmaceutically acceptable salts which may be mentioned are the salts with alkali metals, such as the sodium, potassium and lithium salts, the salts with alkaline earth metals, such as the magnesium salt, the ammonium salt and the addition salts with organic nitrogen bases such as ethanolamine, diethanolamine, trimethylamine, triethylamine, methylamine, propylamine, diisopropylamine, N,N-dimethylethanolamine, benzylamine, dibenzylamine, dicyclohexylbenzylamine, N-benzyl-$\beta$-phenethylamine, N,N'-dibenzylethylenediamine, benzhydrylamine, arginine, leucine, lysine or N-methylglucamine.

Pharmaceutically acceptable salts which may be mentioned for the products of the general formula (V) in which Z represents a radical of the general formula (VII) in which $R_4$ represents a trialkylammonio radical are the quaternary ammonium salts corresponding to the anions listed above.

The examples which follow, which are given without implying a limitation, show how the invention can be put into practice. The NMR spectra of the products illustrated in these examples and in the reference examples thereafter have general characteristics which are common to all the products of the general formula (I) or of the general formula (V) and particular characteristics which are peculiar to each of the products according to the substituents. In Example 1 and also in Reference Examples 1 and 16, the assignment of all the protons in the molecule is given; in the following examples or reference examples, only the particular characteristics due to the variable radicals are mentioned. For the products of the general formula (I), all the protons are designated according to the numbering indicated in the following formula:

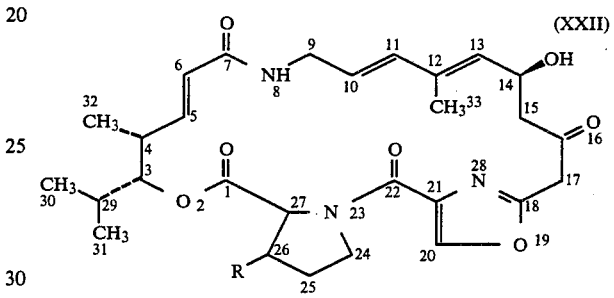

For the synergistines of the general formula (V), all the protons are designated according to the numbering indicated in the general formula (XXIII); this numbering is that recommended by J. O. ANTEUNIS et al. [Eur. J. Biochem., 58, 259 (1975)].

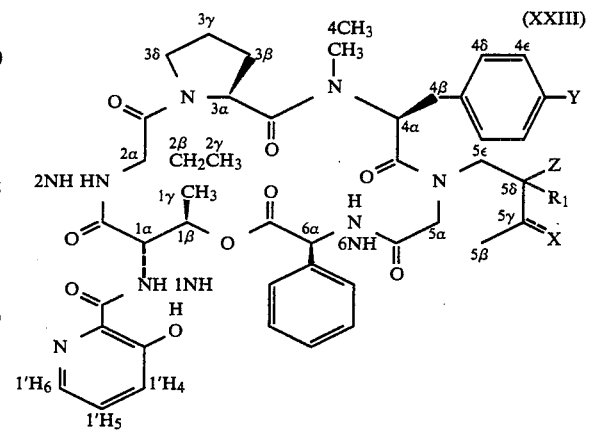

All the spectra were run at 250 MHz in deuterochloroform; the chemical shifts are expressed in ppm relative to the signal for tetramethylsilane. The abbreviations used below are as follows:
s=singlet
d=doublet
t=triplet
mt=multiplet
up=unresolved peaks
dd=doublet of doublets
dt=doublet of triplets
ddd=doublet of doublet of doublets
dddd=doublet of doublet of doublet of doublets In the examples which follow, "flash" chromatography is understood as meaning a purification technique which comprises using a short chromatography column and operating under a moderate pressure (50 kPa) using a silica of particle size 40–53 μm, according to W. C. STILL, M. KAHN and A. MITRA [J. Org. Chem., 43, 2933 (1978)].

EXAMPLE 1

A solution of diethylaminoethanethiol (3.7 g) in methylene chloride (15 cc) is added to a suspension of pristinamycin II$_A$ (13.1 g) in methanol (150 cc). The solution obtained is stirred for 18 hours at a temperature of the order of 20° C. and then poured into distilled water (1500 cc); the mixture obtained is extracted 3 times with methylene chloride (1000 cc in total). The organic phases are combined, dried over magnesium sulphate and filtered and the filtrate is then concentrated to dryness under reduced pressure (2.7 kPa) at 30° C. The residue obtained is purified by "flash" chromatography [eluent: chloroform/methanol (90/10 by volume)]; after concentration to dryness of fractions 5 to 23 under reduced pressure (2.7 kPa) at 30° C., 26-(2-dimethylaminoethyl)thiopristinamycin II$_B$ (12.4 g) is obtained in the form of a yellow powder melting at about 105° C.

| δ(ppm) | Shape | Assignment |
|---|---|---|
| 8.10 | s | H 20 |
| 6.60 | s broad | NH 8 |
| 6.55 | dd | H 5 |
| 6.15 | d | H 11 |
| 5.80 | dd | H 6 |
| 5.65 | ddd | H 10 |
| 5.50 | d | H 13 |
| 4.95 | ddd | H 14 |
| 4.77 | dd | H 3 |
| 4.75 | d | H 27 |
| 4.27 | ddd | H 24 |
| 4.05 | ddd | H 9 |
| 3.87 | ddd | H 9 |
| 3.80 | s | H 17 |
| 3.55 | ddd | H 24 |
| 3.40 | ddd | H 26 |
| 3.10 | dd } ABX | H 15 |
| 2.9 | dd } System | H 15 |
| 2.75 | s | —S—C$\underline{H}_2$CH$_2$— |
| 2.74 | up | H 4 |
| 2.60 | q | —N—(C$\underline{H}_2$CH$_3$)$_2$ |
| 2.15 to 1.85 | up | H 25, H 29 |
| 1.70 | s | H 33 |
| 1.05 | up | —N(CH$_2$C$\underline{H}_3$)$_2$ + H 32 |
| 0.95 | dd | H 30 + H 31 |

A 2% aqueous solution of 26-(2-diethylaminoethyl)-thiopristinamycin II$_B$ (product BA) in the form of the hydrochloride is obtained with:
product BA: 0.1 g
0.05N hydrochloric acid: 3 cc
distilled water: q.s. 5 cc

EXAMPLE 2

By following a procedure analogous to that described in Example 1, but starting from pristinamycin II$_A$ (2.7 g) and 2-dimethylaminoethanethiol (0.58 g), and after purification by "flash" chromatography [eluent: chloroform/methanol (90/10 by volume)] and concentration to dryness of fractions 11 to 17 under reduced pressure (2.7 kPa) at 30° C., 26-(2-dimethylaminoethyl)thiopristinamycin II$_B$ (1.1 g) is obtained in the form of a yellow powder melting at about 100° C.

NMR spectrum:

2.35 (s, 6H: —N(CH$_3$)$_2$)

2.80 (up, 4H: —S—C$\underline{H}_2$C$\underline{H}_2$—N$\diagup^{\diagdown}$)

3.40 (ddd, 1H: H 26)
4.75 (d, 1H: H 27)
8.10 (s, 1H: H 20)

A 2% aqueous solution of 26-(2-dimethylaminoethyl)thiopristinamycin II$_B$ (product BB) in the form of the hydrochloride is obtained with:
product BB: 0.1 g
0.1N hydrochloric acid: 1.6 cc
distilled water: q.s. 5 cc

EXAMPLE 3

By following a procedure analogous to that described in Example 1, but starting from pristinamycin II$_A$ (5.25 g) and 3-dimethylaminopropanethiol (1.3 g), and after purification by "flash" chromatography [eluent: chloroform/methanol (90/10 by volume)] and concentration to dryness of fractions 6 to 29 under reduced pressure (2.7 kPa) at 30° C., 26-(3-dimethylaminopropyl)thiopristinamycin II$_B$ (3.3 g) is obtained in the form of a yellow powder melting at about 100° C.

NMR spectrum:

1.50 (s, 3H × 0.5: H 33 1st isomer)
1.70 (s, 3H × 0.5: H 33 2nd isomer)

1.80 (up, 2H: —SCH$_2$—C$\underline{H}_2$—CH$_2$N$\diagup^{\diagdown}$)

2.20 (s, 6H × 0.5: —N(CH$_3$)$_2$ 1st isomer)
2.25 (s, 6H × 0.5: —N(CH$_3$)$_2$ 2nd isomer)

2.40 (up, 2H: —SC$\underline{H}_2$—CH$_2$—CH$_2$N$\diagup^{\diagdown}$)

2.70 (up, 2H: —SCH$_2$—CH$_2$—C$\underline{H}_2$N$\diagup^{\diagdown}$)

3.35
3.45 } (2 up, 1H: H 26 of each isomer)

4.60
4.70 } (2 d, 1H: H 27 of each isomer)

7.80
8.10 } (2 s, 1H: H 20 of each isomer)

A 3.3% aqueous solution of 26-(3-dimethylaminopropyl)thiopristinamycin II$_B$ (product BC) is obtained with:
product BC: 0.1 g
0.1N hydrochloric acid: 1.55 cc

EXAMPLE 4

By following a procedure analogous to that described in Example 1, but starting from pristinamycin $II_A$ (5.25 g) and 2-(pyrrolidin-1-yl)ethanethiol (1.7 g), and after purification by "flash" chromatography [eluent: chloroform/methanol (95/5 by volume)] and concentration to dryness of fractions 19 to 60 under reduced pressure (2.7 kPa) at 30° C., 26-[2-(pyrrolidin-1-yl)ethyl]thiopristinamycin $II_B$ (3.9 g) is obtained in the form of a yellow powder melting at about 115° C.

NMR spectrum:

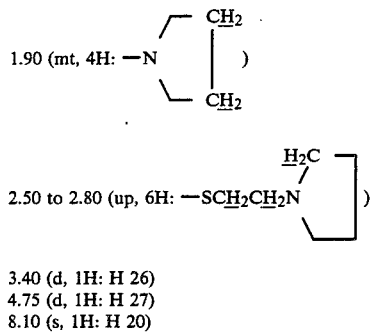

3.40 (d, 1H: H 26)
4.75 (d, 1H: H 27)
8.10 (s, 1H: H 20)

A 5% aqueous solution of 26-[2-(pyrrolidin-1-yl)ethyl]thiopristinamycin $II_B$ (product BD) in the form of the hydrochloride is obtained with:
product BD: 0.1 g
0.1N hydrochloric acid: 1.5 cc
distilled water: q.s. 2 cc The 2-(pyrrolidin-1-yl)ethanethiol can be prepared according to the method described by J. W. HAEFFELE and R. W. BROGE, Proc. Sci. Toilet Goods Assoc. 32, 52 (1959) [Chem. Abstr. 54, 17234e (1960)].

EXAMPLE 5

By following a procedure analogous to that described in Example 1, but starting from pristinamycin $II_A$ (3.15 g) and 1-(2-mercaptoethyl)-4-methylpiperazine (1.1 g), and after purification by "flash" chromatography [eluent: chloroform/methanol (95/5 by volume)] and concentration to dryness of fractions 14 to 20 under reduced pressure (2.7 kPa) at 30° C., 26-[2-(4-methylpiperazin-1-yl)ethyl]thiopristinamycin $II_B$ (1.4 g) is obtained in the form of a yellow powder melting at about 115° C.

NMR spectrum:

2.30 (s, 3H: $\diagdown$N—CH$_3$)

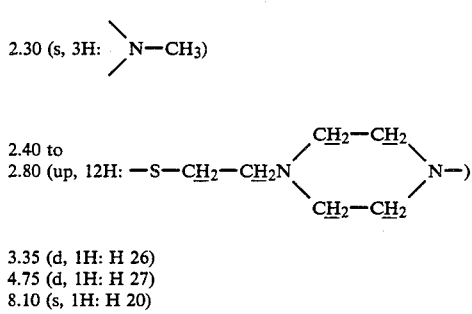

3.35 (d, 1H: H 26)
4.75 (d, 1H: H 27)
8.10 (s, 1H: H 20)

A 2% aqueous solution of 26-[2-(4-methylpiperazin-1-yl)ethyl]thiopristinamycin $II_B$ (product BE) in the form of the hydrochloride is obtained with:
product BE: 0.1 g
0.1N hydrochloric acid: 1.46 cc
distilled water: q.s. 5 cc The 1-(2-mercaptoethyl)-4-methylpiperazine can be prepared according to the method described by D. D. REYNOLDS et al., J. Org. Chem., 26, 5125 (1961).

EXAMPLE 6

By following a procedure analogous to that described in Example 1, but starting from pristinamycin $II_A$ (3.15 g) and 1-diethylaminopropane-2-thiol (1.8 g), and after purification by "flash" chromatography [eluent: methylene chloride/methanol (90/10 by volume)] and concentration to dryness of fractions 3 to 5 under reduced pressure (2.7 kPa) at 30° C., 26-(1-diethylaminoprop-2-yl)thiopristinamycin $II_B$ (1.4 g) is obtained in the form of a yellow powder melting at about 160° C.

| NMR spectrum: |
| --- |
| 1 (up, 9H: H 32 + —N(CH$_2$CH$_3$)$_2$) |
| 2.50 (up, 6H: —CH$_2$N(CH$_2$CH$_3$)$_2$) |
| 3.30 (up, 1H: H 26) |
| 4.70 (d, 1H: H 27) |
| 8.12 (s, 1H: H 20) |

A 5% aqueous solution of 26-(1-diethylaminoprop-2-yl)thiopristinamycin $II_B$ (product BF) in the form of the hydrochloride is obtained with:
product BF: 20 mg
0.1N hydrochloric acid: 0.3 cc
distilled water: q.s. 0.4 cc The 1-diethylaminopropane-2-thiol can be prepared by the method described by R. T. WRAGG, J. Chem. Soc. (C), 16, 2087 (1969).

EXAMPLE 7

By following a procedure analogous to that described in Example 1, but starting from pristinamycin $II_A$ (3.15 g) and 1-methylpiperidine-4-thiol (1.6 g) and adding triethylamine (0.6 g) to the reaction mixture, and after purification by "flash" chromatography [eluent: methylene chloride/methanol (92/8 by volume)] and concentration to dryness of fractions 4 to 20 under reduced pressure (2.7 kPa) at 30° C., 26-(1-methylpiperidin-4-yl)thiopristinamycin $II_B$ (0.9 g) is obtained in the form of a yellow powder melting at about 180° C.

NMR spectrum:

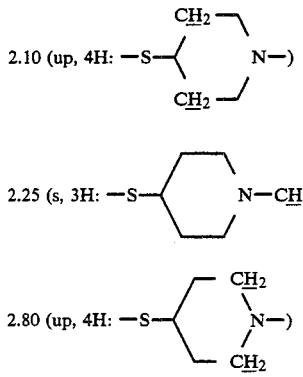

-continued
3.55 (up, 1H: H 26)
4.62 (up, 1H: H 27)
7.70 (up, 1H: H 8)
8.10 (s, 1H: H 20)

A 5% aqueous solution of 26-(1-methylpiperidin-4-yl)thiopristinamycin II$_B$ (product BG) in the form of the hydrochloride is obtained with:
product BG: 10 mg
hydrochloride acid: 0.14 cc
distilled water: q.s. 2 cc The 1-methylpiperidine-4-thiol can be prepared by the method described by H. BARRER and R. E. LYLE, J. Org. Chem., 27, 641 (1962).

EXAMPLE 8

By following a procedure analogous to that described in Example 1, but starting from pristinamycin II$_A$ (5.25 g) and a 5N ethanolic solution of gaseous dimethylamine (10 cc), and after purification by "flash" chromatography [eluent: chloroform/methanol (90/10 by volume)] and concentration to dryness of fractions 14 to 24 under reduced pressure (2.7 kPa) at 30° C., 26-dimethylaminopristinamycin II$_B$ (0.8 g) is obtained in the form of a yellow powder melting at about 230° C.

| NMR spectrum (CDCl$_3$ + 10% of CD$_3$OD): |
| --- |
| 2.35 (s, 6H: —N(CH$_3$)$_2$) |
| 3.25 (d, 1H: H 26) |
| 5.05 (d, 1H: H 27) |
| 8.20 (s, 1H: H 20) |

A 2% aqueous solution of 26-dimethylaminopristinamycin II$_B$ (product BH) in the form of the hydrochloride is obtained with:
product BH: 0.1 g
0.1N hydrochloric acid: 1.75 cc
distilled water: q.s. 5 cc

EXAMPLE 9

By following a procedure analogous to that described in Example 1, but starting from pristinamycin II$_A$ (5.25 g) and 4-methylpiperazine (5 g), and after purification by "flash" chromatography [eluent: chloroform/methanol (90/10 by volume)] and concentration to dryness of fractions 20 to 44 under reduced pressure (2.7 kPa) at 30° C., 26-(4-methylpiperazin-1-yl)pristinamycin II$_B$ (0.7 g) is obtained in the form of a yellow powder melting at about 140° C.

NMR spectrum:

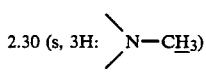
2.30 (s, 3H: N—CH$_3$)

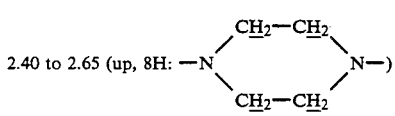
2.40 to 2.65 (up, 8H: —N(CH$_2$—CH$_2$)$_2$N—)

3.40 to 3.70 (up containing H 26)
5.75 (d, 1H: H 27)
8.10 (s, 1H: H 20)

A 3.3% aqueous solution of 26-(4-methylpiperazin-1-yl)pristinamycin II$_B$ (product BI) in the form of the hydrochloride is obtained with:
product BI: 0.1 g
0.1N hydrochloric acid: 1.6 cc
distilled water: q.s. 3 cc

EXAMPLE 10

A solution of pristinamycin II$_A$ (5.2 g) in 1-methylpiperazine (20 cc) is stirred for 1 hour 30 minutes at a temperature of the order of 20° C. and is then poured into distilled water (600 cc). The emulsion obtained is extracted 3 times with methylene chloride (600 cc in total); the organic phases are combined, dried over magnesium sulphate and filtered and the filtrate is then concentrated to dryness under reduced pressure (2.7 kPa) at 30° C. The residue obtained is purified by "flash" chromatography [eluent: chloroform/methanol (90/10 by volume)]; after concentration to dryness of fractions 13 to 30 under reduced pressure (2.7 kPa) at 30° C., 26-(4-methylpiperazin-1-yl)pristinamycin II$_B$ (2.6 g) is obtained in the form of a beige powder melting at about 140° C.

The NMR spectrum of this product is identical to that of the product described in Example 9.

EXAMPLE 11

By following a procedure analogous to that described in Example 1, but starting from pristinamycin II$_A$ (12.6 g) and 2,3-bisdimethylaminopropanethiol (5.2 g), and after purification by "flash" chromatography [eluent: methylene chloride/methanol (90/10 by volume)] and concentration to dryness of fractions 29 to 42 under reduced pressure (2.7 kPa) at 30° C., 26-(2,3-bisdimethylaminopropyl)thiopristinamycin II$_B$ (0.3 g) is obtained in th form of a yellow powder melting at about 110° C.

NMR spectrum:

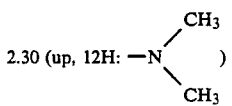
2.30 (up, 12H: —N(CH$_3$)$_2$)

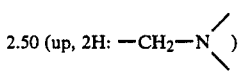
2.50 (up, 2H: —CH$_2$—N)

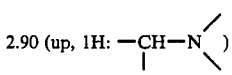
2.90 (up, 1H: —CH—N)

3.56 (up, 1H: H 26)
4.64 (d, 1H: H 27)
4.66 (d, 1H: H 27)
7.81 (s, 1H: H 20)

A 2% aqueous solution of 26-(2,3-bisdimethylaminopropyl)thiopristinamycin II$_B$ (product BJ) in the form of the hydrochloride is obtained with:
product BJ: 10 mg
0.1N hydrochloric acid: 0.14 cc
distilled water: q.s. 0.5 cc The 2,3-bisdimethylaminopropanethiol can be prepared according to the method described by H. NISHIMURA and H. TAKAMATSU, Yakugaku Zasshi, 84, 944 (1964) (Chem. Abstr. 62, 2750 b (1965)).

REFERENCE EXAMPLE 1

Pristinamycin $I_A$ (0.5 g) and sodium cyanoborohydride (20 mg) are added to a solution of 3-dimethylaminopropylamine (0.41 cc) in methanol (15 cc) containing a 2N methanolic solution of hydrogen chloride (2.4 cc), kept at 55° C. The solution obtained is subsequently allowed to return to a temperature of the order of 20° C. for about 2 hours and is then concentrated to dryness under reduced pressure (2.7 kPa) at 30° C. The residue obtained is triturated with a mixture of methylene chloride (50 cc) and a saturated aqueous solution of sodium bicarbonate (50 cc); the organic phase is decanted and the aqueous phase is extracted twice with methylene chloride (20 cc in total). The organic phases are combined, dried over magnesium sulphate and filtered and the filtrate is then concentrated to dryness under reduced pressure (2.7 kPa) at 30° C. The residue obtained is purified by "flash" chromatography [eluent: chloroform/methanol (80/20 by volume)]. Fractions 15 to 30 are combined and concentrated to dryness under reduced pressure (2.7 kPa) at 30° C.; the residue obtained is triturated with ethyl ether (5 cc), filtered off and dried under reduced pressure (0.027 kPa) at 20° C. This gives 5γ-deoxy-5γ-(3-dimethylaminopropyl)aminopristinamycin $I_A$ (60 mg) in the form of a cream powder melting at about 160° C.

The complete NMR spectrum has the following characteristics:

| δ(ppm) | Shape of the signal | Assignment |
| --- | --- | --- |
| 8.40 | d | 6 NH |
| 8.25 | d | 1 NH |
| 7.55 | dd | 1'H₆ |
| 7.05 | up | 6γ + 6δ + 6ε |
| 7 | dd | 1'H₄ |
| 6.90 | dd | 1'H₅ |
| 6.70 | d | } 4δ + 4ε |
| 6.40 | d | |
| 6.50 | d | 2 NH |
| 5.75 | ddd | 1β |
| 5.45 | d | 6α |
| 5.25 | dd | 4α |
| 5 | s (broad) | 5α |
| 4.75 | dd | 1α |
| 4.60 | up | 2α |
| 4.45 | d (broad) | 5ε₁ |
| 4.40 | dd | 3α |
| 3.4 | dd (broad) | 3δ₁ |
| 3.20 | dd (broad) | 3δ₂ |
| 3 | s | 4 CH₃ |
| 3 | up | 5γ + 4β₁ and 2 |
| 2.80 | s | 4 N(CH₃)₂ |
| 2.65 | t | —NCH₂—(chain) |
| 2.35 | up | 5ε₂ + 5β₁ |
| 2.25 | t | —NCH₂—(chain) |
| 2.20 | s | —N(CH₃)₂(chain) |
| 1.60 | up | —CH₂—(chain) 2β + 3γ |
| 1.25 | d | 1γ |
| 0.90 | t | 2γ |
| 0.50 | dddd | 5β₂ |

A 10% aqueous solution of 5γ-deoxy-5γ-(3-dimethylaminopropyl)aminopristinamycin $I_A$ (product A) in the form of the hydrochloride is obtained with:
product A: 0.1 g
2N hydrochloric acid: 0.52 cc
distilled water: q.s. 1 cc By following a procedure analogous to that described in Reference Example 1, the following synergistines of the general formula (V) are prepared, which can be associated with the products according to the invention [the symbols ____, Z and $R_1$ are defined as under (1) for the general formula (V)]:

| Reference example | Y | X | (1) M.p. (2) Solubility |
| --- | --- | --- | --- |
| 2 | —N(CH₃)₂ | —NH(CH₂)₂N(CH₃)₂ | (1) yellow powder m.p. about 180° C. (2) 10% in aqueous solution as the hydrochloride |
| 3 | —N(CH₃)₂ | 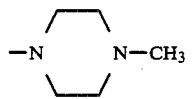 —N⟨ ⟩N—CH₃ | (1) white powder m.p. about 195° C. (2) 10% in aqueous solution as the hydrochloride |
| 4 | —N(CH₃)₂ | 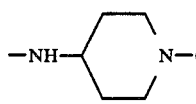 —NH—⟨ ⟩N—CH₃ | (1) beige powder m.p. about 195° C. (2) 3.7% in aqueous solution as the hydrochloride |
| 5 | —N(CH₃)₂ | —NHOH | (1) white powder m.p. about 170° C. (2) 10% in aqueous solution as the hydrochloride |
| 6 | —N(CH₃)₂ | —NH(CH₂)₃OH | (1) cream powder m.p. about 160° C. (2) 2% in aqueous solution as the hydrochloride |
| 7 | —H | —NH(CH₂)₃N(CH₃)₂ | (1) beige powder m.p. about 140° C. (2) 10% in aqueous solution as the hydrochloride |

REFERENCE EXAMPLE 8

A 5N ethanolic solution of dimethylamine (2.8 cc) and then a 5N methanolic solution of hydrogen chloride (2 cc) are added to a solution of pristinamycin $I_A$ (2 g) in methanol (25 cc). Sodium cyanoborohydride (76 mg) is added to the resulting solution and the mixture is then stirred for 48 hours at a temperature of the order of 20° C. The reaction mixture is then concentrated to dryness under reduced pressure (2.7 kPa) at 30° C. The residue is triturated with a mixture of methylene chloride (25 cc) and a saturated aqueous solution of sodium bicarbonate (25 cc); the organic phase is decanted and the aqueous phase is extracted twice with methylene chloride (50 cc in total). The organic phases are combined, dried over magnesium sulphate and filtered and the filtrate is then concentrated to dryness under reduced pressure (2.7 kPa) at 30° C. The residue is purified by "flash" chromatography [eluent: chloroform/methanol (92/8 by volume)]. Fractions 5 to 12 are combined and concentrated to dryness under reduced pressure (2.7 kPa) at 30° C. This gives 5γ-deoxy-5γ-dimethylaminopristinamycin $I_A$ (0.7 g) in the form of a beige powder melting at about 170° C.

| NMR spectrum: |
| --- |
| 0.70 (dt, 1H: 5β_2) |
| 2.10 to 2.60 (up, 4H: 5δ_1 + 5δ_2 + 5β_1 + 5γ) |
| 2.15 (s, 3H × 0.8: —N(CH_3)_2 1st isomer) |
| 2.20 (s, 3H × 0.2: —N(CH_3)_2 2nd isomer) |

A 2% aqueous solution of 5γ-deoxy-5γ-dimethylaminopristinamycin $I_A$ (product B) in the form of the hydrochloride is obtained with:
product B: 0.05 g
0.1N hydrochloric acid: 0.56 cc
distilled water: q.s. 2.5 cc

REFERENCE EXAMPLE 9

By following a procedure analogous to that described in Reference Example 8, 5γ-deoxy-5γ-methylaminopristinamycin $I_A$ (0.35 g) is obtained in the form of a yellow powder melting at about 185° C.

A 1% aqueous solution of 5γ-deoxy-5γ-methylaminopristinamycin $I_A$ in the form of the hydrochloride is obtained.

REFERENCE EXAMPLE 10

By following a procedure analogous to that described in Reference Example 8, 5γ-deoxy-5γ-[N-(2-dimethylaminoethyl)-N-methylamino]pristinamycin $I_A$ (1.2 g) is obtained in the form of a white powder melting at about 120° C.

A 10% aqueous solution of 5γ-deoxy-5γ-[N-(2-dimethylaminoethyl)-N-methylamino]pristinamycin $I_A$ (product D) in the form of the hydrochloride is obtained.

REFERENCE EXAMPLE 11

A 3 Å molecular sieve (5 g) is added to a solution of pristinamycin $I_A$ (3 g), 4-diethylamino-1-methylbutylamine (3.3 g), sodium cyanoborohydride (0.11 g) and a 5N methanolic solution of hydrogen chloride (9 cc) in methanol (75 cc). The suspension obtained is stirred for 4 days at a temperature of the order of 20° C. and then filtered; the filtrate is concentrated to dryness under reduced pressure (2.7 kPa) at 30° C. The residue is triturated with a mixture of methylene chloride (50 cc) and a saturated aqueous solution of sodium bicarbonate (50 cc); the organic phase is decanted and the aqueous phase is extracted twice with methylene chloride (50 cc in total). The organic phases are combined, dried over magnesium sulphate and filtered and the filtrate is then concentrated to dryness under reduced pressure (2.7 kPa) at 30° C. The residue is purified by "flash" chromatography [eluent: chloroform/methanol (90/10 by volume)]. This gives 5γ-deoxy-5γ-(4-diethylamino-1-methylbutyl)aminopristinamycin $I_A$ (0.7 g) in the form of a beige powder melting at about 160° C.

NMR spectrum:

1.10 (mt, 9H: —N(CH_2C$\underline{H}$_3)_2 + —CH—C$\underline{H}$_3)
  | about 1.7 (up, 4H: —C$\underline{H}$_2—C$\underline{H}$_2—CH_2—N(C_2H_5)_2)
2.90 (up, 6H: —C$\underline{H}$_2N(C$\underline{H}$_2CH_3)_2)

7.70 (mt, 1H × 0.45: 1'H_6 1st isomer)
7.77 (mt, 1H × 0.55: 1'H_6 2nd isomer)

A 10% aqueous solution of 5γ-deoxy-5γ-(4-diethylamino-1-methylbutyl)aminopristinamycin $I_A$ (product F) in the form of the hydrochloride is obtained with:
product F: 0.1 g
0.1N hydrochloric acid: q.s. 1 cc

REFERENCE EXAMPLE 12

Sodium cyanoborohydride (0.7 g) is added to a solution of 5γ-deoxy-5γ-hydroxyiminopristinamycin $I_A$ (12.5 g) in methanol (300 cc) containing a 2N methanolic solution of hydrogen chloride (10 cc). The solution obtained is stirred for 2 days at a temperature of the order of 20° C. and then concentrated to dryness under reduced pressure (2.7 kPa) at 30° C. The residue is triturated in a mixture of methylene chloride (200 cc) and a saturated aqueous solution of sodium bicarbonate (100 cc); the organic phase is decanted and the aqueous phase is extracted with methylene chloride (100 cc). The organic phases are combined, dried over magnesium sulphate and filtered and the filtrate is concentrated to dryness under reduced pressure (2.7 kPa) at 30° C. After purification by "flash" chromatography [eluent: chloroform/methanol (95/5 by volume)], 5γ-deoxy-5γ-hydroxyaminopristinamycin $I_A$ (6.8 g) is obtained in the form of a white powder melting at about 170° C.

| NMR spectrum: 0.4 (up, 1H: 5β_2); 2.45 (d, 1H: 5β_2); |
| --- |
| 3.1 (d: 5γ in complex unresolved peaks); 7.80 (mt, 1H × 0.75: 1'H_6 1st isomer); 7.95 (mt, 1H × 0.25: 1'H_6 2nd isomer). |

The 5γ-deoxy-5γ-hydroxyiminopristinamycin $I_A$ can be obtained by stirring a solution of pristinamycin $I_A$ (15 g) and hydroxylamine hydrochloride (7.5 g) in methanol (150 cc) containing a 2N methanolic solution of hydrogen chloride (8 cc), for 5 hours, at a temperature of the order of 20° C. The reaction mixture is then concentrated to dryness under reduced pressure (2.7 kPa) at 30° C. The residue is triturated with a mixture of chloroform (100 cc) and a saturated aqueous solution of sodium bicarbonate (100 cc); the organic phase is decanted and the aqueous phase is extracted twice with chloroform (200 cc in total). The organic phases are combined, dried over magnesium sulphate and filtered and the filtrate is concentrated to dryness under reduced pressure (2.7 kPa) at 30° C. This gives 5γ-deoxy-5γ-hydroxyiminopristinamycin $I_A$ (14 g) in the form of a beige powder melting at 210° C.

| NMR spectrum: |
| --- |
| 0.35 (dd, 1H: 5β_2) |
| 3.25 (up, 2H: 4ε_2 + 5β_1) |
| 5.05 (d, 1H: 5α) |
| 5.5 (up, 2H including 5ε_1) |
| 7.80 (dd, 1H × 0.40: 1'H_6 1st isomer) |
| 7.90 (dd, 1H × 0.60: 1'H_6 2nd isomer) |

REFERENCE EXAMPLE 13

By following a procedure analogous to that described in Reference Example 11, 5γ-[N-(carboxymethyl)methylamino]-5γ-deoxypristinamycin I$_A$ (0.8 g) is obtained in the form of a cream powder melting at about 140° C.

A 2% aqueous solution of 5γ-[N-(carboxymethyl)methylamino]-5γ-deoxypristinamycin I$_A$ (product K) is obtained with:
  product K: 0.2 g
  distilled water: q.s. 10 cc

REFERENCE EXAMPLE 14

Acetyl chloride (0.3 cc) is added to a solution of 5γ-deoxy-5γ-(2-dimethylaminoethyl)aminopristinamycin I$_A$ (3.2 g) in chloroform (50 cc) containing triethylamine (0.6 cc). The reaction mixture is stirred for 30 minutes at a temperature of the order of 20° C. and then concentrated to dryness under reduced pressure (2.7 kPa) at 30° C. The residue is purified by "flash" chromatography [eluent: chloroform/methanol (90/10 by volume)]; by concentration to dryness of fractions 10 to 21 under reduced pressure (2.7 kPa) at 30° C., 5γ-deoxy-5γ-[N-(2-dimethylaminoethyl)acetamido]pristinamycin I$_A$ (1.8 g) is obtained in the form of a white powder melting at about 170° C.

NMR spectrum:
0.9 (up, 4H: 2γ + 5β$_2$)
2.05 to 2.15 (up, 3H: 5δ$_1$ + 5δ$_2$ + 5γ)
2.15 (s, 3H: —COCH$_3$)
2.45 (s, 6H: —N(CH$_3$)$_2$)

2.35 to 2.60 (up, 5H: 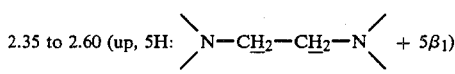 + 5β$_1$)

7.8 (mt, 1H × 0.75: 1'H$_6$ 1st isomer)
8.25 (mt, 1H × 0.25: 1'H$_6$ 2nd isomer)

A 10% aqueous solution of 5γ-deoxy-5γ-[N-(2-dimethylaminoethyl)acetamido]pristinamycin I$_A$ (product L) in the form of the hydrochloride is obtained with:
  product L: 0.1 g
  0.2N hydrochloric acid: 0.51 cc
  distilled water: q.s. 1 cc The 5γ-deoxy-5γ-(2-dimethylaminoethyl)aminopristinamycin I$_A$ can be prepared as described in Example 5.

REFERENCE EXAMPLE 15

By following a procedure analogous to that described in Reference Example 14, 5γ-deoxy-5γ-[N-(3-dimethylaminopropyl)acetamido]pristinamycin I$_A$ (1.6 g) is obtained in the form of an ochre powder melting at 210° C.

A 10% aqueous solution of 5γ-deoxy-5γ-[N-(3-dimethylaminopropyl)acetamido]pristinamycin I$_A$ (product M) in the form of the hydrochloride is obtained.

REFERENCE EXAMPLE 16

3-Dimethylaminopropanethiol (1.95 g) is added to a solution of 5δ-methylenepristinamycin I$_A$ (3.6 g) in a mixture of methanol (25 cc) and chloroform (5 cc) and the solution obtained is then stirred for 20 hours at a temperature of the order of 20° C. The reaction mixture is then poured into distilled water (250 cc); the emulsion obtained is extracted 3 times with methylene chloride (250 cc in total). The organic phases are combined, dried over magnesium sulphate and filtered and the filtrate is then concentrated to dryness under reduced pressure (2.7 kPa) at 30° C. The residue obtained is purified by "flash" chromatography [eluent: chloroform/methanol (95/5 by volume)]; fractions 10 to 38 are concentrated to dryness under reduced pressure (2.7 kPa) at 30° C. The residue obtained is triturated in ethyl ether (30 cc); the crystals obtained are filtered off and then dried under reduced pressure (27 Pa) at 20° C. This gives 5δ-(3-dimethylaminopropyl)thiomethylpristinamycin I$_A$ (2.4 g) in the form of white crystals melting at 234° C.

| NMR spectrum: | | |
|---|---|---|
| δ(ppm) | Shape | Assignment |
| 11.65 | s (broad) | OH |
| 8.70 | d | 6 NH |
| 8.40 | d | 1 NH |
| 7.80 | dd | 1'H$_6$ |
| 7.45 | up | 1'H$_4$ + 1'H$_5$ |
| 7.27 | up | |
| 7.17 | up | 6γ + 6δ + 6ε |
| 7.05 | d ⎫ | |
| 6.60 | d ⎭ AB system | 4δ + 4ε |
| 6.47 | d | 2 NH |
| 5.87 | ddd | 1β |
| 5.83 | d | 6α |
| 5.24 | up | 5α + 4α |
| 5.03 | ddd | 5ε$_1$ |
| 4.85 | dd | 1α |
| 4.80 | up | 2α |
| 4.53 | dd | 3α |
| 3.53 | up | 3δ$_1$ |
| 3.35 | dd ⎫ | |
| 3.15 | dd ⎭ ABX system | —CH$_2$—S—CH$_2$— |
| 3.25 | s | 4 NCH$_3$ |
| 3.25 | up | 3δ$_2$ |
| 2.90 | s | 4 N(CH$_3$)$_2$ |
| 2.90 | up | 4β |
| 2.55 | t | —CH$_2$N(CH$_3$)(CH$_3$) |
| 2.50 | dd | 5ε$_2$ |
| 2.40 | t | —CH$_2$SCH$_2$— |
| 2.40 to 2.20 | up | 5δ + 5β$_1$ |
| 2.25 | s | —CH$_2$N(CH$_3$)$_2$ |
| 2 | up | 3β$_1$ |
| 1.75 | up | —SCH$_2$CH$_2$CH$_2$— |
| 1.8 to 1.45 | up | 2β$_1$ + 2β$_2$ + 3γ$_1$ |
| 1.30 | d | 1γ |
| 1.25 to 1.05 | up | 3γ$_2$ + 3β$_2$ |
| 0.9 | t | 2γ |
| 0.60 | dd | 5β$_2$ |

A 10% aqueous solution of 5δ-(3-dimethylaminopropyl)thiomethylpristinamycin I$_A$ (product AA) is obtained with:
  product AA: 30 mg
  0.1N hydrochloric acid: q.s. 0.3 cc The 5δ-methylenepristinamycin I$_A$ can be prepared in the following manner:

Sodium cyanoborohydride (0.43 g) is added to a solution of 5δ-dimethylaminomethylenepristinamycin I$_A$ (12 g) in tetrahydrofuran (230 cc) containing trifluoroacetic acid (1.2 cc). The solution obtained is stirred for 4 hours at a temperature of the order of 20° C. and is then concentrated to dryness under reduced pressure (2.7 kPa) at 30° C. The residue obtained is purified by "flash" chromatography [eluent: chloroform/methanol (95/5 by volume)]; fractions 4 to 15 are concentrated to dryness under reduced pressure (2.7 kPa) at 30° C. This gives 5δ-methylenepristinamycin I$_A$ (5.5 g) in the form of white crystals melting at 245° C.

NMR spectrum:
0.55 (dd, 1H: 5β$_2$)
2.40 (d, 1H: 5β$_1$)
3.55 (dd, 1H: 5ε$_1$)
5.25 (up, 2H: 5α + 5ε$_1$)

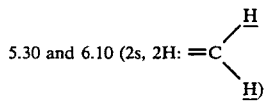

5.30 and 6.10 (2s, 2H: =C$\begin{smallmatrix}H\\H\end{smallmatrix}$)

7.85 (dd, 1H: 1'H$_6$)

The 5δ-dimethylaminomethylenepristinamycin I$_A$ can be prepared in the following manner:

Tert.-butoxybis(dimethylamino)methane (230 cc) is added to a solution of pristinamycin I$_A$ (46 g) in 1,2-dichloroethane (460 cc); the solution obtained is stirred for 18 hours at a temperature of the order of 20° C. The reaction mixture is diluted with methylene chloride (1 liter) and then washed 3 times with a 0.4% aqueous solution of ammonium chloride (3 liters in total). The organic phase is dried over magnesium sulphate and filtered and the filtrate is then concentrated to dryness under reduced pressure (2.7 kPa) at 30° C. The residue obtained is triturated with distilled water (600 cc); the mixture is filtered and the solid product is dried under reduced pressure (2.7 kPa) at 20° C. This gives crude 5δ-dimethylaminomethylenepristinamycin I$_A$ (41 g) in the form of a beige powder. This product is of sufficient quality to be used as such in the subsequent stages. However, it can be purified in the following manner:

Crude 5δ-dimethylaminomethylenepristinamycin I$_A$ (23.5 g) is purified by "flash" chromatography [eluent: chloroform/methanol (98/2 by volume)]. Fractions 16 to 25 are combined and concentrated to dryness under reduced pressure (2.7 kPa) at 30° C. This gives 5δ-dimethylaminomethylenepristinamycin I$_A$ (12 g) in the form of a beige powder melting at about 195° C.

| NMR spectrum: |
| --- |
| 0.9 (t, 3H: 2γ) |
| 1.0 (dd, 1H: 5β$_2$) |
| 2.50 (d, 1H: 5β$_1$) |
| 3.10 (s, 6H: —N(CH$_3$)$_2$) |
| 3.70 (d, 1H: 5ε$_2$) |
| 5.50 (d, 1H: 5ε$_1$) |
| 7.40 (s, 1H: =CHN(CH$_3$)$_2$) |
| 7.75 (dd, 1H: 1'H$_6$) |

REFERENCE EXAMPLE 17

By following a procedure analogous to that described in Reference Example 16, but starting from 5δ-methylenevirginiamycin S (0.9 g) and 3-dimethylaminopropanethiol (0.52 g), and after purification by "flash" chromatography [eluent: chloroform/methanol (90/10 by volume)] and concentration to dryness of fractions 13 to 25 under reduced pressure (2.7 kPa) at 30° C, 5δ-(3-dimethylaminopropyl)thiomethylvirginiamycin S (0.3 g) is obtained in the form of a white powder melting at about 142° C.

NMR spectrum:
0.45 (dd, 1H: 5β$_2$)

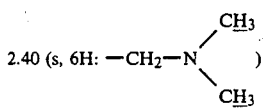

1.90 (up, 2H: —SCH$_2$CH$_2$CH$_2$N$\diagup\diagdown$)

2.40 (s, 6H: —CH$_2$—N$\begin{smallmatrix}CH_3\\CH_3\end{smallmatrix}$)

2.60 (up, 4H: —S—CH$_2$—CH$_2$—CH$_2$—N$\diagup\diagdown$)

3.45 (d, 1H: 5ε$_2$)
4.85 (up, 3H including 5ε$_1$)
5.25 (dd, 1H: 5α)
7.78 (dd, 1H: 1'H$_6$)

A 10% aqueous solution of 5δ-(3-dimethylaminopropyl)thiomethylvirginiamycin S (product AB) in the form of the hydrochloride is obtained with:
 product AB: 0.1 g
 hydrochloric acid: q.s. 1 cc The 5δ-methylenevirginiamycin S can be prepared in a manner analogous to that described in Reference Example 16 for 5δ-methylenepristinamycin I$_A$, but starting from 5δ-dimethylaminomethylenevirginiamycin S (2 g) and sodium cyanoborohydride (74 mg). After purification by "flash" chromatography [eluent: chloroform/methanol (98/2 by volume)] and concentration to dryness of fractions 2 to 5 under reduced pressure (2.7 kPa) at 30° C., 5δ-methylenevirginiamycin S (1 g) is obtained in the form of a beige powder melting at about 190° C.

NMR spectrum:
0.35 (dd, 1H: 5β$_2$)
2.45 (dd, 1H: 5β$_1$)
3.55 (dd, 1H: 5ε$_2$)
5.25 (dd, 1H: 5ε$_1$)
5.25 (up, 1H: 5α)

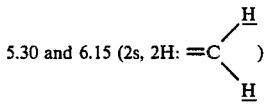

5.30 and 6.15 (2s, 2H: =C$\begin{smallmatrix}H\\H\end{smallmatrix}$)

7.75 (dd, 1H: 1'H$_6$)

The 5δ-dimethylaminomethylenevirginiamycin S can be obtained by following a procedure analogous to that described in Reference Example 16 for 5δ-dimethylaminomethylenepristinamycin I$_A$, but starting from virginiamycin S (2 g) and bis(dimethylamino)tert.-butoxymethane (10 cc), and after purification by "flash" chromatography [eluent: chloroform/methanol (98/2 by volume)] and concentration to dryness of fractions 9 to 12 under reduced pressure (2.7 kPa) at 30° C., 5δ-dimethylaminomethylenevirginiamycin S (0.8 g) is obtained in the form of a yellow powder melting at about 175° C.

NMR spectrum:
0.9 (up, 4H: 2γ + 5β$_2$)
3.05 (s, 6H: =CH—N(CH$_3$)$_2$)

-continued
3.65 (d, 1H: 5ε₂)
4.85 (d, 1H: 5ε₁)
5.15 (dd, 1H: 5α)

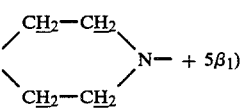

7.10 to 7.40 (up: aromatic protons + =CH—N )

7.70 (dd, 1H: 1'H₆)

REFERENCE EXAMPLE 18

By following a procedure analogous to that described in Reference Example 16, but starting from 5δ-methylenepristinamycin I$_A$ (6 g) and 2-(4-methylpiperazin-1-yl)ethanethiol (4 cc), and after purification by "flash" chromatography [eluent: chloroform/methanol (97/3 by volume)] and concentration to dryness of fractions 8 to 20 under reduced pressure (2.7 kPa) at 30° C., 5δ-[2-(4-methylpiperazin-1-yl)ethyl]thiomethylpristinamycin I$_A$ (2.6 g) is obtained in the form of white crystals melting at 216° C.

NMR spectrum:
0.60 (dd, 1H: 5β₂)

2.27 (s, 3H: \N—CH₃)

2.40 to 2.80 (up, 11H: —CH₂—N⟨CH₂—CH₂⟩N— + 5β₁)
                            ⟨CH₂—CH₂⟩

5.05 (dd, 1H: 5ε₁)
5.27 (up, 2H: 5α + 4α)
7.85 (mt, 1H × 0.8: 1'H₆ 1st isomer)
7.95 (mt, 1H × 0.2: 1'H₆ 2nd isomer)

A 5% aqueous solution of 5δ-[2-(4-methylpiperazin-1-yl)ethyl]thiomethylpristinamycin I$_A$ (product AC) in the form of the hydrochloride is obtained with:
product AC: 0.1 g
0.1N hydrochloric acid: 0.96 cc
distilled water: q.s. 2 cc

REFERENCE EXAMPLE 19

By following a procedure analogous to that described in Reference Example 16, but starting from 5δ-methylenepristinamycin I$_A$ (2 g) and 3-(4-methylpiperazin-1-yl)propanethiol (3 cc), and after purification by "flash" chromatography [eluent: chloroform/methanol (90/10 by volume)] and concentration to dryness of fractions 10 to 25 under reduced pressure (2.7 kPa) at 30° C., 5δ-[3-(4-methylpiperazin-1-yl)propyl]thiomethylpristinamycin I$_A$ (1.9 g) is obtained in the form of a white powder melting at about 156° C.

NMR spectrum:
0.65 (dd, 1H: 5β₂)

2.30 (s, 3H: \N—CH₃)

2.50 (up, 13H: —CH₂N⟨CH₂CH₂⟩N— + —SCH₂— + 5β₁)
                       ⟨CH₂CH₂⟩

5.27 (up, 2H: 5α + 4α)
7.85 (dd, 1H × 0.8: 1'H₆ 1st isomer)
7.95 (dd, 1H × 0.2: 1'H₆ 2nd isomer)

A 10% aqueous solution of 5δ-[3-(4-methylpiperazin-1-yl)propyl]thiomethylpristinamycin I$_A$ (product AD) in the form of the hydrochloride is obtained with:
product AD: 0.1 g
0.5N hydrochloric acid: 0.38 cc
distilled water: q.s. 1 cc

REFERENCE EXAMPLE 20

By following a procedure analogous to that described in Reference Example 16, but starting from 5δ-methylenepristinamycin I$_A$ (4 g) and 1,3-bis(dimethylamino)-propane-2-thiol (4 cc), and after purification by "flash" chromatography [eluent: chloroform/methanol (95/5 by volume)] and concentration to dryness of fractions 20 to 60 under reduced pressure (2.7 kPa) at 30° C., 5δ-[1,3-bis-(dimethylamino)prop-2-yl]thiomethylpristinamycin I$_A$ (0.59 g) is obtained in the form of a white powder melting at about 170° C.

NMR spectrum:
0.63 (dd, 1H: 5β₂)
2.40 (s, 6H: —N(CH₃)₂)

2.50 (up, 10H: —CH⟨CH₂N⟩ + —N(CH₃)₂)
                     ⟨CH₂N⟩

4.97 (s, 1H: 5ε₁)
5.30 (up, 2H: 5α + 4α)
7.85 (mt, 1H × 0.85: 1'H₆ 1st isomer)
7.95 (mt, 1H × 0.15: 1'H₆ 2nd isomer)

A 7.5% aqueous solution of 5δ-[1,3-bis(dimethylamino)prop-2-yl]thiomethylpristinamycin I$_A$ (product AE) in the form of the hydrochloride is obtained with:
product AE: 0.03 g
0.1N hydrochloric acid: 0.3 cc
distilled water: q.s. 0.4 cc

REFERENCE EXAMPLE 21

By following a procedure analogous to that described in Reference Example 16, but starting from 5δ-methylenepristinamycin I$_A$ (3 g) and 1-methyl-4-mercaptopiperidine (0.97 g), and after purification by "flash" chromatography [eluent: chloroform/methanol (95/5 by volume)] and concentration to dryness of fractions 10 to 16 under reduced pressure (2.7 kPa) at 30° C., 5δ-(1-methylpiperidin-4-yl)thiomethylpristinamycin I$_A$ (1.1 g) is obtained in the form of a white powder melting at 260° C.

NMR spectrum:
0.6 (dd, 1H: 5β₂)

-continued 2 (up, 4H: —S—<CH₂—\N—CH₂—/ N—))

2.20 (s, 3H: —S—<ring>N—CH₃)

2.35 (up, 1H: 5β₁)

2.90 (up, 4H: —S—<CH₂\N—/CH₂ N—)

5.30 (up, 2H: 5α + 4α)
7.85 (dd, 1H: 1'H₆)

A 5% aqueous solution of 5δ-(1-methylpiperidin-4-yl)thiomethylpristinamycin I_A (product AF) in the form of the hydrochloride is obtained with:
product AF: 0.03 g
0.1N hydrochloric acid: 0.3 cc
distilled water: q.s. 0.6 cc

REFERENCE EXAMPLE 22

By following the procedure of Reference Example 16, but starting from 5δ-methylenepristinamycin I_A (2 g) and 2-diethylaminoethanethiol (0.66 g), and after purification by "flash" chromatography [eluent: chloroform/methanol (95/5 by volume)] and concentration to dryness of fractions 9 to 18 under reduced pressure (2.7 kPa) at 30° C., 5δ-(2-diethylaminoethyl)thiomethylpristinamycin I_A (0.8 g) is obtained in the form of a biege powder melting at 230° C.

NMR spectrum:
0.65 (dd, 1H: 5β₂)
2.38 (d, 1H: 5β₁)

2.3 to 2.8 (up, 8H: —SCH₂CH₂N<CH₂—\CH₂—/ )

3.15 (dd, 1H: —CH₂S—)
3.35 (dd, 1H: —CH₂S—)
5.01 (dd, 1H: 5ε₁)
7.81 (dd, 1H × 0.9: 1'H₆ 1st isomer)
7.90 (dd, 1H × 0.1: 1'H₆ 2nd isomer)

A 5% aqueous solution of 5δ-(2-diethylaminoethyl)-thiomethylpristinamycin I_A (product AF₁) in the form of the hydrochloride is obtained with:
product AF₁: 30 mg
0.1N hydrochloric acid: 0.29 cc
distilled water: q.s. 0.6 cc

REFERENCE EXAMPLE 23

2-Dimethylaminoethylamine (5.3 g) is added dropwise to a solution of 5δ-dimethylaminomethylenepristinamycin I_A (5.5 g) in acetic acid (60 cc) so as not to exceed 25° C. The solution obtained is stirred for 20 hours at a temperature of the order of 20° C. and is then poured slowly into a saturated aqueous solution of sodium bicarbonate; the mixture obtained is extracted twice with methylene chloride (750 cc in total). The organic phases are combined, dried over magnesium sulphate and filtered and the filtrate is concentrated to dryness under reduced pressure (2.7 kPa) at 30° C. The residue is purified by "flash" chromatography [eluent: chloroform/methanol (90/10 by volume)]; fractions 10 to 12 are concentrated to dryness under reduced pressure (2.7 kPa) at 30° C. This gives 5δ-(2-dimethylaminoethyl)aminomethylenepristinamycin I_A (3 g) in the form of a beige powder melting at about 180° C.

NMR spectrum:
0.90 (mt, 4H: 2γ + 5β₂)
2.25 (mt, 6H: —N(CH₃)₂)

2.50 (mt, 3H: —CH₂N<  / + 5β₁)
                       \

3.25 (mt, 2H: 5ε₂ + 3δ₁)
4.90 (mt, 1H: 5ε₁)

between 7.15 and 7.4 (up, 1H: =C<NH—  \H )

9.90 (mt, 1H (exchangeable with D₂O): —NH—)

A 1% aqueous solution of 5δ-(2-dimethylaminoethyl)-aminomethylenepristinamycin I_A (product AG) is obtained with:
product AG: 0.1 g
distilled water: q.s. 10 cc

REFERENCE EXAMPLE 24

By following a procedure analogous to that described in Reference Example 23, but starting from 5δ-dimethylaminomethylenepristinamycin I_A (13.8 g) and 4-amino-1-methylpiperidine (3.4 g), and after purification by "flash" chromatography [eluent: chloroform/methanol (92.5/7.5 by volume)] and concentration to dryness of fractions 15 to 20 under reduced pressure (2.7 kPa) at 30° C., 5δ-(1-methylpiperidin-4-yl)aminomethylenepristinamycin I_A (4.0 g) is obtained in the form of a yellow powder melting at 208° C.

NMR spectrum:
0.40 (up, 4H: 2γ + 2β₂)

2.0 (up, 4H: —<CH₂—\N—CH₂—/ N—)

2.35 (s, 3H: \N—CH₃ /)

2.45 (d, 1H: 5β₁)

2.90 (—<CH₂\N—/CH₂ N—)

-continued 3.20 (under unresolved peaks, 1H: —C$\underline{H}$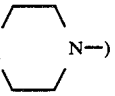N—)

3.50 (d, 1H: 5ε$_2$)
4.85 (under unresolved peaks, 1H: 5ε$_1$)
6.65 (d, 1H: =CHNH—)
9.70 (dd, 1H × 0.15: =CH—N$\underline{H}$— 1st isomer)
10.03 (dd, 1H × 0.85: =CH—N$\underline{H}$— 2nd isomer)

A 10% aqueous solution of 5δ-(1-methylpiperidin-4-yl)aminomethylenepristinamycin I$_A$ (product AT) in the form of the hydrochloride is obtained with:

product AT: 0.03 g
0.1N hydrochloric acid: 0.3 cc
distilled water: q.s. 0.3 cc

The 4-amino-1-methylpiperidine can be prepared by the method described by E. F. ELSLAGER, L. M. WERBEL, A. CURRY, N. HEADEN and J. JOHNSON, J. Med. Chem. 17, 99 (1974).

By following the procedure of Reference Example 23, the following synergistines of the general formula (V) are prepared, which can be associated with the products according to the invention [the symbols , X and Z are defined as under 2b) for the general formula (V) and, unless stated otherwise, Y represents a dimethylamino radical]:

| Reference example | R$_4$ | (1) M.p. <br> (2) Solubility |
|---|---|---|
| 25 | —NH—(CH$_2$)$_2$N(C$_2$H$_5$)$_2$ | (1) yellow powder m.p. about 150° C. <br> (2) 5% in aqueous solution as the hydrochloride |
| 26 | —NH(CH$_2$)$_2$NHCH$_3$ | (1) yellow powder m.p. = 174° C. <br> (2) 1% in aqueous solution as the hydrochloride |
| 27 | —NH(CH$_2$)$_3$N(CH$_3$)$_2$ | (1) yellow powder m.p. about 155° C. <br> (2) 6.6% in aqueous solution as the hydrochloride |
| 28 | —NH—CH(CH$_3$)—CH$_2$N(CH$_3$)$_2$ | (1) yellow powder m.p. abount 160° C. <br> (2) 1% in aqueous solution as the hydrochloride |
| 29 | —NHCH$_2$CH(CH$_3$)—N(CH$_3$)$_2$ | (1) orange powder m.p. about 175° C <br> (2) 10% in aqueous solution as the hydrochloride |
| 30 | —NH—CH(CH$_3$)—(CH$_2$)$_3$N(C$_2$H$_5$)$_2$ | (1) beige powder m.p. about 160° C. <br> (2) 1% in aqueous solution as the hydrochloride |
| 31 | —NH—(CH$_2$)$_2$—N(pyrrolidinyl) | (1) yellow powder m.p. = 183° C. <br> (2) 1% in aqueous solution as the hydrochloride |
| 32 | —NH(CH$_2$)$_3$—N(pyrrolidinyl) | (1) yellow powder m.p. = 170° C. <br> (2) 1% in aqueous solution |
| 33 | —NH—(CH$_2$)$_2$—N(piperidinyl) | (1) yellow powder m.p. 162° C. <br> (2) 1% in aqueous solution as the hydrochloride |
| 34 | —NH(CH$_2$)$_2$—N(morpholinyl) | (1) beige powder m.p. about 172° C. <br> (2) 1% in aqueous solution as the hydrochloride |

-continued

| Reference example | R$_4$ | (1) M.p. (2) Solubility |
|---|---|---|
| 35 | —NH—CH$_2$—[pyrrolidine with N-CH$_2$CH$_3$] | (1) beige powder m.p. about 160° C. (2) 1% in aqueous solution as the hydrochloride |
| 36 | —NH—[piperidine with N-CH$_3$] | (1) beige powder m.p. = 177° C. (2) 1% in aqueous solution as the hydrochloride |
| 37 (H) | —NH—[piperazine ring]—N—CH$_3$ | (1) beige powder m.p. about 195° C. (2) 5% in aqueous solution as the hydrochloride |
| 38 —N(CH$_3$)$_2$ | —NH(CH$_2$)$_2$—N[piperazine]N—CH$_3$ | (1) yellow powder m.p. = 150° C. (2) 10% in aqueous solution as the hydrochloride |
| 39 —N(CH$_3$)$_2$ | —NH—(CH$_2$)$_2$—[imidazole ring with N, NH] | (1) yellow powder m.p. = 138° C. (2) 10% in aqueous solution as the hydrochloride |

REFERENCE EXAMPLE 40

2-Dimethylaminoethanethiol (2.1 g) is added to a solution of 5δ-dimethylaminomethylenepristinamycin I$_A$ (1.84 g) in acetic acid (40 cc). The solution obtained is stirred for 20 hours at a temperature of the order of 20° C. and is then poured slowly into a saturated aqueous solution of sodium bicarbonate; the mixture obtained is extracted 3 times with methylene chloride (400 cc in total). The organic phases are combined, dried over magnesium sulphate and filtered and the filtrate is concentrated to dryness under reduced pressure (2.7 kPa) at 30° C. The residue obtained is purified by "flash" chromatography [eluent: chloroform/methanol (96/4 by volume)]; fractions 5 and 6 are combined and concentrated to dryness under reduced pressure (2.7 kPa) at 30° C. This gives 5δ-(2-dimethylaminoethyl)thiomethylenepristinamycin I$_A$ (0.8 g) in the form of a yellow powder melting at about 150° C.

NMR spectrum
0.68 (dd, 1H: 5β$_2$)
2.32 (s, 6H × 0.85: —CH$_2$N(CH$_3$)$_2$ 1st isomer)
2.35 (s, 6H × 0.15: —CH$_2$N(CH$_3$)$_2$ 2nd isomer)
2.45 (d, 1H: 5β$_1$)
2.65 (mt, 2H: —SCH$_2$—)
3.05 (t, 2H: —CH$_2$N⟨ )
3.43 (dd, 1H: 5ε$_2$)
5.15 (in unresolved peaks: 5ε$_1$)
7.60 (s broad, 1H: =CHS—)
7.83 (mt, 1H: 1'H$_6$ two isomers)

A 1% aqueous solution of 5δ-(2-dimethylaminoethyl)thiomethylenepristinamycin I$_A$ (product AX) in the form of the hydrochloride is obtained with:
product AX: 0.1 g
0.1N hydrochloric acid: 1 cc
distilled water: q.s. 10 cc By following the procedure of Reference Example 40, the following synergistines of the general formula (V) are prepared, which can be associated with the products according to the invention [the symbols ——, X and Z are defined as under (2b) for the general formula (V) and, unless stated otherwise, Y represents a dimethylamino radical]:

| Reference example | Y | R$_4$ | (1) M.p. (2) Solubility |
|---|---|---|---|
| 41 | —N(CH$_3$)$_2$ | —S—(CH$_2$)$_2$N(C$_2$H$_5$)$_2$ | (1) beige powder m.p. about 192° C. (2) 1% in aqueous solution as the hydrochloride |
| 42 | —N(CH$_3$)$_2$ | —S—(CH$_2$)$_3$N(CH$_3$)$_2$ | (1) beige powder m.p. about 170° C. (2) 1% in aqueous solution as the |

-continued

| Reference example | Y | R₄ | (1) M.p. (2) Solubility |
|---|---|---|---|
| 43 | —H | —S(CH₂)₃N(CH₃)₂ | (1) beige powder m.p. about 140° C. (2) 10% in aqueous solution as the hydrochloride |
| 44 | —N(CH₃)₂ | —SCH₂—CH(CH₃)—CH₂N(CH₃)₂ | (1) beige powder m.p. = 234° C. (2) 1% in aqueous solution as the hydrochloride |
| 45 | —N(CH₃)₂ | —S—CH₂—C(CH₃)₂—N(CH₃)₂ | (1) beige powder m.p. about 200° C. (2) 1% in aqueous solution as the hydrochloride |
| 46 | —N(CH₃)₂ | —S(CH₂)₂—N(azetidinyl) | (1) beige powder m.p. about 180° C. (2) 1% in aqueous solution as the hydrochloride |
| 47 | | —S—(CH₂)₂—(N-methylpyrrolidinyl) | (1) beige powder m.p. about 215° C. (2) 0.6% in aqueous solution as the hydrochloride |
| 48 | | —S—(1-methylpiperidin-4-yl) | (1) yellow powder m.p. about 170° C. (2) 1% in aqueous solution as the hydrochloride |
| 49 | | —S—(1-ethylpiperidin-3-yl) | (1) beige powder m.p. about 175° C. (2) 1% in aqueous solution as the hydrochloride |
| 50 | | —S—(CH₂)₂N(CH₃)—(CH₂)₂N(CH₃)₂ | (1) yellow powder m.p. about 160° C. (2) 1% in aqueous solution |
| 51 | | —S—CH[CH₂N(CH₃)₂]₂ | (1) beige powder m.p. about 190° C. (2) 1% in aqueous solution as the hydrochloride |
| 52 | | —S(CH₂)₂—N(piperazinyl)N—CH₃ | (1) beige powder m.p. about 170° C. (2) 1% in aqueous solution as the hydrochloride |
| 53 | | —S(CH₂)₃—N(piperazinyl)N—CH₃ | (1) beige powder m.p. about 190° C. (2) 10% in aqueous solution as the hydrochloride |
| 54 | | —S—CH₂CH(CH₃)—CH₂N(CH₃)₃⁺ | (1) ochre powder m.p. about 150° C. (2) 1% in aqueous solution as the hydrochloride |
| 55 | | —S(CH₂)₂SO₃H | (1) yellow powder m.p. >280° C. (2) 5% in aqueous |

REFERENCE EXAMPLE 56

A solution of 5δ-(4-methylphenyl)sulphonyloxymethylenepristinamycin $I_A$ (5.2 g) in methylene chloride (50 cc) is added to a solution of 1-(2-mercaptopropyl)-4-methylpiperazine (0.87 g) in ethanol (50 cc) to which sodium ethylate (0.34 g) has been added. The reaction mixture is stirred for 16 hours at a temperature of the order of 20° C. and then diluted with methylene chloride (500 cc) and distilled water (100 cc). After stirring, the aqueous phase is extracted twice with methylene chloride (50 cc in total). The organic phases are combined, dried over magnesium sulphate and filtered and the filtrate is then concentrated to dryness under reduced pressure (2.7 kPa) at 30° C. The residue is purified by "flash" chromatography [eluent: chloroform/methanol (97.5/2.5 by volume)]. Fractions 33 to 80 are combined and concentrated to dryness under reduced pressure (2.7 kPa) at 30° C. This gives 5δ-[3-(4-methylpiperazin-1-yl)prop-2-yl]thiomethylenepristinamycin $I_A$ (1.25 g) in the form of a beige powder melting at about 195° C.

NMR spectrum:
0.70 (dd, 1H: 5β₂)

1.25 (d, 3H: —CH—C$\underline{H}$₃)
            |

2.30 (s, 3H: \N—C$\underline{H}$₃)

2.50 (up, 10H: —C$\underline{H}$₂—N⟨CH₂CH₂/CH₂CH₂⟩N—CH₃)

3.40 (dd, 1H: 5ε₂)
7.85 (dd broad, 1H: 1'H₆)

A 10% aqueous solution of 5δ-[3-(4-methylpiperazin-1-yl)prop-2-yl]thiomethylenepristinamycin $I_A$ (product AAN) in the form of the hydrochloride is obtained with:

product AAN: 0.03 g
  0.1N hydrochloric acid: 0.3 cc

The 1-(2-mercaptopropyl)-4-methylpiperazine is prepared by heating a mixture of propylene sulphide (19 cc) and N-methylpiperazine (29 cc) at 100° C. for 16 hours. This gives a colourless oil (32 g) distilling at 105° C. under 1.3 kPa.

The 5δ-(4-methylphenyl)sulphonyloxymethylenepristinamycin $I_A$ can be obtained in the following manner:

Triethylamine (0.42 cc) and then p-toluenesulphonyl chloride (0.57 g) are added, at a temperature of the order of −30° C., to a solution of 5δ-hydroxymethylenepristinamycin $I_A$ (2.7 g) in methylene chloride (30 cc). The reaction mixture is subsequently stirred for 2 hours at a temperature of the order of 20° C. and then concentrated to dryness under reduced pressure (2.7 kPa) at 30° C.; the residue obtained is purified by "flash" chromatography [eluent: methylene chloride/methanol (96/4 by volume)]. After concentration to dryness of fractions 4 to 6 under reduced pressure (2.7 kPa) at 30° C., 5δ-(4-methylphenyl)sulphonyloxymethylenepristinamycin $I_A$ (2.2 g) is obtained in the form of a white powder melting at about 265° C.

NMR spectrum:
0.50 (dd, 1H: 5β₂)

2.35 (s, 3H: 

3.30 (dd, 1H: 5ε₂)
5.25 (d, 1H: 5α)
5.30 (dd, 1H: 5ε₁)
7.35 to 7.90 (AB system + up, 8H: 4δ + 4ε +

$$-SO_2-\underset{H\;\;H}{\overset{H\;\;H}{\bigcirc}}-CH_3)$$

7.85 (dd, 1H: 1'H₆)

The 5δ-hydroxymethylenepristinamycin $I_A$ can be prepared in the following manner:

5δ-Dimethylaminomethylenepristinamycin $I_A$ (10.6 g) is added, with stirring, to a 0.1N aqueous solution of hydrochloric acid (420 cc). The solution obtained is then stirred for 3 hours at a temperature of the order of 20° C. A saturated aqueous solution of sodium bicarbonate (30 cc) is then added dropwise so as to give a pH of the order of 4. The product which precipitates is filtered off and then washed 3 times with distilled water (30 cc in total). After drying under reduced pressure (2.7 kPa) at a temperature of the order of 20° C., 5δ-hydroxymethylenepristinamycin $I_A$ (9.5 g) is obtained in the form of a beige powder. This product is of sufficient quality to be used as such in the subsequent stages. However, it can be purified in the following manner:

Crude 5δ-hydroxymethylenepristinamycin $I_A$ (9.5 g) is dissolved in ethyl acetate (50 cc); the solution obtained is poured onto silica gel (100 g) contained in a column of diameter 2.8 cm. Elution is carried out initially with ethyl acetate (400 cc) and the corresponding eluate is discarded; elution is continued with ethyl acetate (1600 cc) and the corresponding eluate is concentrated to dryness under reduced pressure (2.7 kPa) at 30° C. This gives 5δ-hydroxymethylenepristinamycin $I_A$ (6.3 g) in the form of white crystals melting at 220° C.

NMR spectrum:
0.69 (dd, 1H: 5β₂)
2.43 (d, 1H: 5β₁)
3.40 (d, 1H: 5ε₂)

-continued

NMR spectrum:
4.0 to 4.2 (up, 3H: $4\alpha + 5\epsilon_1 + 5\alpha$)
8.15 (s, 1H: =C$\underline{H}$—OH)
11.63 (s broad, 1H: =CH—O$\underline{H}$)

REFERENCE EXAMPLE 57

By following a procedure analogous to that described in Reference Example 56, 5δ-(3-dimethylaminoprop-2-yl)thiomethylenepristinamycin I$_A$ (1 g) is obtained in the form of a yellow powder melting at 172° C.

A 5% aqueous solution of 5δ-(3-dimethylaminoprop-2-yl)thiomethylenepristinamycin I$_A$ (product AAO) in the form of the hydrochloride is obtained.

REFERENCE EXAMPLE 58

By following a procedure analogous to that described in Reference Example 56, 5δ-(5-diethylaminopent-2-yl)thiomethylenepristinamycin I$_A$ (1.32 g) is obtained in the form of a beige powder melting at about 185° C.

A 10% aqueous solution of 5δ-(5-diethylaminopent-2-yl)thiomethylenepristinamycin I$_A$ (product AAP) in the form of the hydrochloride is obtained.

REFERENCE EXAMPLE 59

A solution of 5δ-[(4-methylphenyl)sulphonyloxymethylene]pristinamycin I$_A$ (7.6 g) in tetrahydrofuran (60 cc) is cooled to a temperature of the order of −10° C. A solution of 2-dimethylaminoethanol (0.65 g) in tetrahydrofuran (60 cc), to which a 50% dispersion of sodium hydride in mineral oil (0.35 g) has been added, is added slowly to the first solution, the temperature of −10° C. being maintained. When the addition has ended, the temperature is allowed to rise slowly to about 20° C. The reaction mixture is stirred for 24 hours at this temperature and then diluted with methylene chloride (500 cc) and washed with a saturated solution of ammonium chloride (2×50 cc). The organic phase is dried over magnesium sulphate and filtered and the filtrate is then concentrated to dryness under reduced pressure (2.7 kPa) at 40° C. The residue obtained is purified by "flash" chromatography [eluent: chloroform/methanol (95/5 by volume)]. Fractions 12 to 17 are combined and concentrated to dryness under reduced pressure (2.7 kPa) at 25° C. This gives 5δ-(2-dimethylaminoethoxymethylene)pristinamycin I$_A$ (1.5 g) in the form of a beige powder melting at about 160° C.

NMR spectrum:
0.65 (dd, 1H: $5\beta_2$)
2.3 (s, 6H: —N(C$\underline{H}_3$)$_2$)

2.65 (up, 2H: —C$\underline{H}_2$N$\diagup_\diagdown$ )

3.42 (dd, 1H: $5\epsilon_2$)
4.15 (t, 2H: —OC$\underline{H}_2$—)
5.15 (d, 1H: $5\epsilon_1$)

7.45 (under the aromatic protons, 1H: $\diagdown$C=C$\underline{H}$O—)$\diagup$ 7.80 (dd, 1H: 1'H$_6$)

A 1% aqueous solution of 5δ-(2-dimethylaminoethoxymethylene)pristinamycin I$_A$ (product AAQ) in the form of the hydrochloride is obtained with:
 product AAQ: 0.03 g
 0.1N hydrochloric acid: 0.3 cc
 distilled water: q.s. 3 cc The present invention also provides pharmaceutical compositions comprising a compound of the formula (I), in the free form or, preferably, in the form of an addition salt with a pharmaceutically acceptable acid, in association with a known synergistine or, preferably, a synergistine of the formula (V), it being possible for the association also to contain any other pharmaceutically compatible product which is inert or physiologically active. The compositions of the invention can be administered parenterally, orally, rectally or topically.

The sterile compositions for parenteral administration can preferably be suspensions, emulsions or aqueous or non-aqueous solutions. Water, propylene glycol, a polyethylene glycol, vegetable oils, in particular olive oil, injectable organic esters, e.g. ethyl oleate, or other suitable organic solvents can be employed as the solvent or vehicle. These compositions can also contain adjuvants, in particular wetting agents, agents for imparting isotonicity, emulsifiers, dispersants and stabilizers. Sterilization can be carried out in several ways, e.g. by filtration under aseptic conditions, by incorporating sterilizing agents into the composition, by irradiation or by heating. The compositions can also be prepared in the form of sterile solid compositions which can be dissolved in an injectable sterile medium at the time of use.

Tablets, pills, powders or granules can be used as solid compositions for oral administration. In these compositions, the active product according to the invention (if appropriate in association with another pharmaceutically compatible product) if mixed with one or more inert diluents or adjuvants such as sucrose, lactose or starch. These compositions can also comprise substances other than diluents, e.g. a lubricant such as magnesium stearate.

Solutions, suspensions, syrups and elixirs containing inert diluents such as water or paraffin oil, and pharmaceutically acceptable emulsions, can be used as liquid compositions for oral administration. These compositions can also comprise substances other than diluents, e.g. wetting, sweetening or flavouring products.

The compositions for rectal administration are suppositories or rectal capsules, which contain, in addition to the active principle, excipients such as cocoa butter, semi-synthetic glycerides or polyethylene glycols.

The compositions for topical administration can be e.g. creams, ointments, lotions, eye lotions, mouthwashes, nose drops or aerosols.

In human therapy, the products according to the invention, in association with known synergistines or, preferably, with synergistines of the general formula (V), are particularly useful in the treatment of infections of bacterial origin. The doses depend on the desired effect and the duration of the treatment; for an adult, they are generally between 500 and 2000 mg per day, administered parenterally, in particular intravenously by slow perfusion, the dose of synergistine of the general formula (V) also being between 500 and 2000 mg per day.

In general, the physician will determine the dosage which he considers to be most appropriate as a function of the age, the weight and all the other factors peculiar to the subject to be treated.

The examples which follow, which are given without implying a limitation, illustrate compositions according to the invention.

EXAMPLE A

An injectable solution for perfusion, containing 5 g/liter of active mixture and having the following composition, is prepared by the usual technique:

26-(2-diethylaminoethyl)thiopristinamycin II$_B$: 3 g
5δ-(3-dimethylaminopropyl)thiomethylpristinamycin I$_A$: 2 g
0.1N aqueous solution of hydrochloric acid: 65 cc
distilled water: q.s. 1000 cc

EXAMPLE B

An injectable solution for perfusion, containing 1 g/liter of active mixture and having the following composition, is prepared:

26-(4-methylpiperazin-1-yl)pristinamycin II$_B$: 0.6 g
5δ-[2-(4-methylpiperazin-1-yl)ethyl]thiomethylpristinamycin I$_A$: 0.4 g
0.1N aqueous solution of hydrochloric acid: 15.4 cc
distilled water: q.s. 1000 cc

We claim:

1. A pristinamycin II$_B$ of the formula:

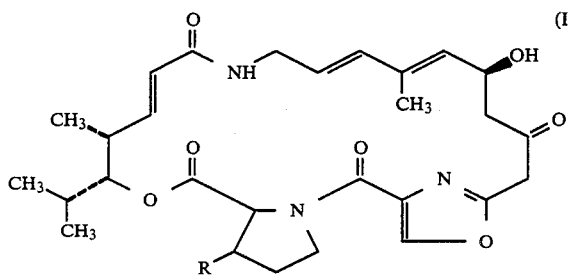

(I)

in which R represents an alkylthio radical substituted by (i) one or two alkylamino or dialkylamino radicals in which the alkyls may be joined together to form, with the nitrogen atom to which they are bonded, a saturated heterocycle chosen from pyrrolidin-1-yl, piperidino, azetidin-1-yl, azepin-1-yl, morpholino, thiomorpholino and piperazin-1-yl, unsubstituted or substituted by an alkyl radical, or (ii) a pyrrolidin-2-yl or pyrrolidin-3-yl, piperidin-2-yl, piperidin-3-yl or piperidin-4-yl, azetidin-2-yl or azetidin-3-yl or azepin-2-yl, azepin-3-yl or azepin-4-yl radical; a radical of the formula:

Het—S— in which Het represents a pyrrolidin-3-yl; piperidin-3-yl or piperidin-4-yl, azetidin-3-yl or azepin-3-yl or azepin-4-yl radical unsubstituted or N-substituted by alkyl; or a dialkylamino radical in which the alkyls may be joined together to form, with the nitrogen atom to which they are bonded, a saturated heterocycle chosen from pyrrolidin-1-yl, piperidino, azetidin-1-yl, azepin-1-yl, morpholino, thiomorpholino and piperazin-1-yl unsubstituted or substituted by an alkyl radical, the aforesaid alkyl radicals and alkyl portions of other radicals containing 1 to 5 carbon atoms each in a straight or branched chain, and its isomeric forms and mixtures thereof, and its pharmaceutically acceptable acid addition salts.

2. A pristinamycin II$_B$ according to claim 1 in which R represents an alkylthio radical substituted by one or two dialkylamino radicals in which the alkyls can be joined to form, with the nitrogen atom to which they are attached, a saturated heterocycle chosen from pyrrolidin-1-yl and piperazin-1-yl unsubstituted or substituted by an alkyl radical; or R represents either a radical of the formula Het—S—in which Het represents a piperidin-4-yl radical unsubstituted or substituted by alkyl, or a dialkylamino radical in which the alkyls can be joined to form, with the nitrogen atom to which they are bonded, a piperazin-1-yl ring unsubstituted or substituted by an alkyl radical, the said alkyl radicals and alkyl portions of radicals being linear or branched and containing 1 to 3 carbon atoms each, and its pharmaceutically acceptable acid addition salts.

3. A pristinamycin II$_B$ according to claim 1 in which R is a branched alkylthio radical of 1 to 3 carbon atoms, substituted by a dialkylamino radical, or R represents a 4-alkylpiperazin-1-yl ring, the said alkyl radicals containing, except where otherwise stated, 1 or 2 carbon atoms each, and its pharmaceutically acceptable acid addition salts.

4. A pristinamycin II$_B$ according to claim 1 which is 26-(1-diethylaminoprop-2-yl)thiopristinamycin II$_B$, and its pharmaceutically acceptable acid addition salts.

5. A pristinamycin II$_B$ according to claim 1 which is 26-(4-methylpiperazin-1-yl)pristinamycin II$_B$.

* * * * *